(12) United States Patent
Tsurumi et al.

(10) Patent No.: US 9,987,386 B2
(45) Date of Patent: Jun. 5, 2018

(54) INSIDE PLUG AND SUCTION-TYPE LIQUID CONTAINER

(71) Applicant: Sumitomo Chemical Company, Limited, Tokyo (JP)

(72) Inventors: Kaoru Tsurumi, Takarazuka (JP); Takahiro Okuie, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 200 days.

(21) Appl. No.: 15/026,658

(22) PCT Filed: Oct. 2, 2014

(86) PCT No.: PCT/JP2014/076396
§ 371 (c)(1),
(2) Date: Apr. 1, 2016

(87) PCT Pub. No.: WO2015/050198
PCT Pub. Date: Apr. 9, 2015

(65) Prior Publication Data
US 2016/0250371 A1    Sep. 1, 2016

(30) Foreign Application Priority Data

Oct. 3, 2013  (JP) ................................. 2013-208596
Jan. 17, 2014  (JP) ................................. 2014-006782

(51) Int. Cl.
*A61L 9/04*  (2006.01)
*A61L 9/12*  (2006.01)
*A01M 1/20*  (2006.01)

(52) U.S. Cl.
CPC ........... *A61L 9/127* (2013.01); *A01M 1/2044* (2013.01); *A01M 1/2077* (2013.01)

(58) Field of Classification Search
CPC .... A01M 1/2044; A01M 1/2077; A61L 9/127
(Continued)

(56) References Cited

U.S. PATENT DOCUMENTS

2004/0074982 A1   4/2004   Kotary et al.
2006/0081721 A1   4/2006   Caserta et al.
(Continued)

FOREIGN PATENT DOCUMENTS

CN    101160141 A     4/2008
CN    202590010 U    12/2012
(Continued)

OTHER PUBLICATIONS

Extended Search Report dated Jun. 7, 2017 in EP Application No. 14850986.2.
(Continued)

*Primary Examiner* — Jason Boeckmann
(74) *Attorney, Agent, or Firm* — Panitch Schwarze Belisario & Nadel LLP

(57) ABSTRACT

An inside plug (10) includes: an inside plug body (12) held at an opening; a liquid absorbent wick holding section (17); and a ring (18) which (i) is held by the liquid absorbent wick holding section (17), (ii) is located in an inner space of a container body (2) in a state where the inside plug body (12) is held at the opening, and (iii) is brought closer to a flat surface (15) by gravity in a case where a suction-type liquid container (1) has fallen sideways.

10 Claims, 15 Drawing Sheets

(58) Field of Classification Search
USPC .............................. 239/34, 44, 45, 46, 50, 51
See application file for complete search history.

(56) References Cited

U.S. PATENT DOCUMENTS

| | | | |
|---|---|---|---|
| 2007/0290066 A1* | 12/2007 | McGee | A01M 1/2044 239/57 |
| 2008/0142613 A1 | 6/2008 | Brown et al. | |
| 2009/0101730 A1* | 4/2009 | Davis | A01M 1/2077 239/44 |

FOREIGN PATENT DOCUMENTS

| | | |
|---|---|---|
| EP | 1877106 A1 | 1/2008 |
| JP | S47-29628 U | 12/1972 |
| JP | S56-176640 U | 12/1981 |
| JP | H 0271545 U | 5/1990 |
| JP | H 09250756 A | 9/1997 |
| JP | H 11253087 A | 9/1999 |
| JP | 2003341756 A | 12/2003 |
| JP | 2004267470 A | 9/2004 |
| JP | 2005-261772 A | 9/2005 |
| JP | 2007261658 A | 10/2007 |
| JP | 2010215273 A | 9/2010 |
| JP | 2011006132 A | 1/2011 |
| WO | 98/00177 A1 | 1/1998 |
| WO | 2006032709 A1 | 3/2006 |

OTHER PUBLICATIONS

Office Action dated Aug. 22, 2017 in JP Application No. 2014-006782 (partial English translation).
Int'l Preliminary Report on Patentability dated Apr. 14, 2016 in Int'l Application No. PCT/JP2014/076396.
Int'l Search Report dated Dec. 22, 2014 in Int'l Application No. PCT/JP2014/076396.
Office Action dated Oct. 26, 2016 in CN Application No. 201480054347.2.

* cited by examiner

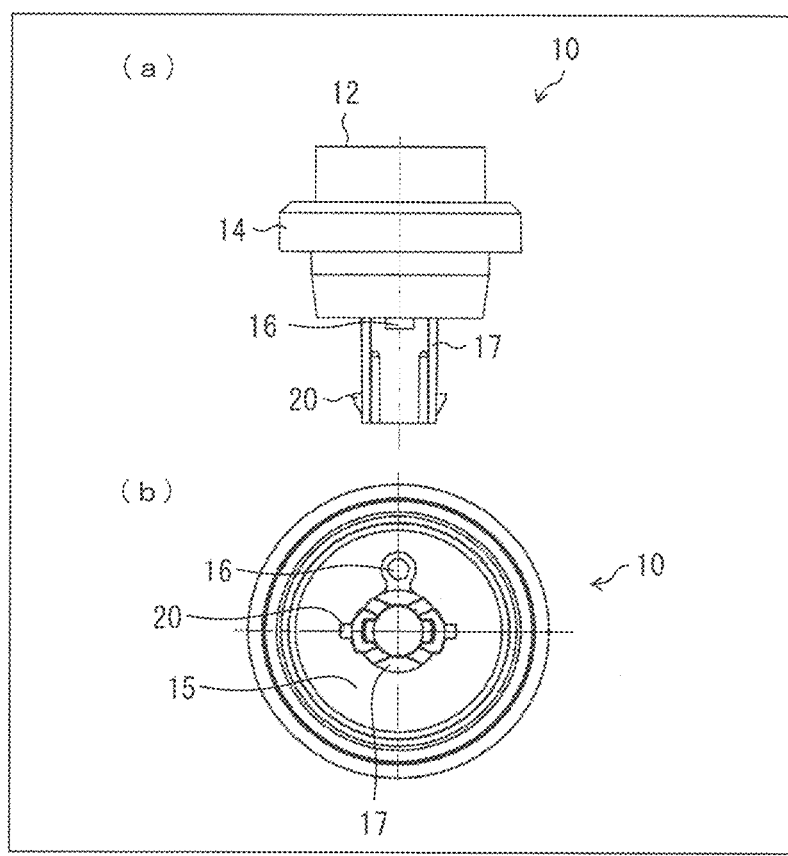

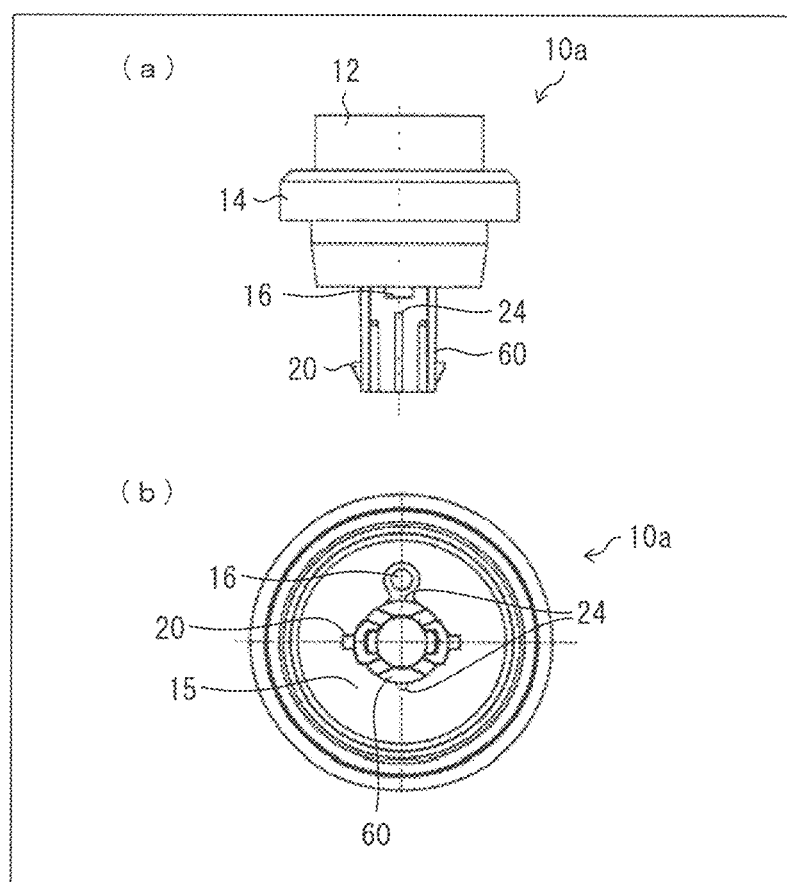

INSIDE PLUG AND SUCTION-TYPE LIQUID CONTAINER

CROSS-REFERENCE TO RELATED APPLICATION

This application is a Section 371 of International Application No. PCT/JP2014/076396 filed Feb. 10, 2014, which was published in the Japanese language on Apr. 9, 2015, under International Publication No. WO 2015/050198 A1, and the disclosure of which is incorporated herein by reference.

TECHNICAL FIELD

The present invention relates to an inside plug and a suction-type liquid container including the inside plug.

BACKGROUND ART

There has been conventionally known a liquid evaporating/diffusing device from which a liquid (e.g., an aromatic etc.) stored in a container body is evaporated and diffused to an outside of the container body by utilizing capillary action which is caused by a liquid absorbent wick that (i) is held by an inside plug and (ii) is made of a porous material such as felt.

According to the liquid evaporating/diffusing device, an opening of the container body, the inside plug, and the liquid absorbent wick are in close contact with each other. Thus, in a case where the inside plug does not have a ventilation structure, a volatilization rate becomes non-uniform due to a change in atmospheric pressure in the container body. Further, in a case where the inside plug does not have a ventilation structure, an atmospheric pressure in the container body may excessively increase due to an influence of a temperature or the like, and this may cause leakage of a liquid via the liquid absorbent wick. For these reasons, a conventional liquid evaporating/diffusing device includes an inside plug having a ventilation structure so as to keep an atmospheric pressure in a container body stable.

Meanwhile, a ventilation hole provided in the inside plug of the liquid evaporating/diffusing device may cause leakage of a liquid via the ventilation hole in a case where the container body has fallen sideways. In regard to this point, the conventional liquid evaporating/diffusing device is configured to prevent leakage of a liquid. Patent Literatures 1 through 3 disclose such a technique for preventing leakage of a liquid.

A liquid storage container of Patent Literature 1 includes (i) a container body for storing therein a liquid, (ii) a holder which is fixed to an opening of a neck section of the container body, and (iii) a felt wick which is held in the holder. The liquid storage container has an air hole which is provided only on one lateral wall side of the holder. Further, the liquid storage container has, in the vicinity of the air hole, a liquid returning groove which communicates with an inside of the container body.

A suction-type container body of Patent Literature 2 includes (i) a container body in which an outside plug is removably attached to an opening of the container body and (ii) a liquid suction wick which is attached to an inside plug held at the opening of the container body. A lower end of the liquid suction-type wick is sunk in a liquid stored in the container body, and an upper end of the liquid suction-type wick is projected outward from an upper end of the inside plug. According to the suction-type container body of Patent Literature 2, a ventilation passage is formed as a recess on an inner peripheral surface of the inside plug. An upper end of the ventilation passage is open upward from an upper end of the inside plug, and a lower end of the ventilation passage communicates with a ventilation hole passing through from inside to outside of the inside plug. Further, an inner surface of the ventilation passage is formed by a liquid suction-type wick.

A liquid absorbent wick holding plug of Patent Literature 3 includes (i) a cylindrical body which is fitted into an opening of a chemical container and (ii) a stopping section which is connected to an end of the cylindrical body. According to the liquid absorbent wick holding plug of Patent Literature 3, (i) a groove is provided on an outer periphery of the cylindrical body and (ii) a ventilation hole which communicates with the groove is provided in the stopping section. In a state where the liquid absorbent wick holding plug is attached to the chemical container, (i) a liquid absorbent wick passes through the cylindrical body and is supported by the cylindrical body and (ii) an inner space of the chemical container communicates with outside air via the groove and the ventilation hole.

CITATION LIST

Patent Literatures

Patent Literature 1
Japanese Patent Application Publication, Tokukai, No. 2003-341756 A (Publication Date: Dec. 3, 2003)
Patent Literature 2
Japanese Patent Application Publication, Tokukaihei, No. 09-250756 A (Publication Date: Sep. 16, 1997)
Patent Literature 3
Japanese Patent Application Publication, Tokukaihei, No. 11-253087 A (Publication Date: Sep. 21, 1999)

SUMMARY OF INVENTION

Technical Problem

However, the techniques of Patent Literatures 1 through 3 relate to a technique for preventing leakage of a liquid by use of a groove, a ventilation passage, or the like which is provided in an inside plug. On the other hand, the inside plug of the present application provides a technique for preventing leakage of a liquid by a new method.

The present invention has been made in view of the problems, and an object of the present invention is to provide (i) an inside plug for preventing leakage of a liquid and (ii) a suction-type liquid container including the inside plug.

Solution to Problem

In order to attain the object, an inside plug in accordance with an aspect of the present invention is an inside plug for holding, at an opening of a container body of a suction-type liquid container, a liquid absorbent wick for sucking up a liquid stored in the container body, the inside plug being inserted in the container body, the inside plug including: an inside plug body which is held at the opening; a liquid absorbent wick holding section for holding the liquid absorbent wick, the liquid absorbent wick holding section being connected to the inside plug body; and a movable section which (i) is located in an inner space of the container body in a state where the inside plug body is held at the opening and (ii) is movable in a direction along the liquid absorbent wick holding section, the inside plug body having, on a liquid-side surface thereof, a through hole through which the inner space of the container body communicates with outside air, the liquid-side surface being a surface of the inside plug body and being located on a side of the liquid stored in the container body, and the movable section being brought closer to the liquid-side surface by gravity in a case where the suction-type liquid container has fallen sideways.

According to the inside plug in accordance with the present invention, the inside plug body has, on the liquid-side surface thereof, the through hole through which the inner space of the container body communicates with outside air. That is, according to the inside plug in accordance with the present invention, the through hole functions as a ventilation structure, and this prevents a decrease in internal pressure of the container body due to absorption of the liquid by a liquid absorbent section. Further, according to the inside plug in accordance with the present invention, the through hole functions as a ventilation structure, and this prevents an increase in internal pressure of the container body due to an increase in temperature or the like. As such, according to the inside plug in accordance with the present invention, the through hole is provided on the liquid-side surface, and this (i) allows the internal pressure of the container body to be stable and (ii) prevents unevenness in diffusion rate of the liquid diffused from the suction-type liquid container.

The inside plug in accordance with the present invention includes the movable section which (i) is located in an inner space of the container body in a state where the inside plug body is held at the opening and (ii) is movable in a direction along the liquid absorbent wick holding section. This allows the inside plug in accordance with the present invention to prevent leakage of a liquid from the suction-type liquid container.

In order to explain the above effect, the following description discusses a case where the suction-type liquid container has fallen sideways.

In general, in a case where (i) there is an air conduit extending from outside to inside of a container body, in other words, air flows from outside to inside of the container body and (ii) a suction-type liquid container has fallen sideways, a liquid stored in the container body easily leaks out from the container body. Thus, in a case where the suction-type liquid container has fallen sideways, air flows from outside to inside of the container body via a through hole provided on a liquid-side surface, and the liquid leaks out from the container body. In a case where a plurality of through holes are provided on the liquid-side surface and the suction-type liquid container has fallen sideways, air flows from outside to inside of the container body via a through hole located above a liquid surface. This causes the liquid to leak out from the container body.

According to the inside plug in accordance with the present invention, however, in a case where the suction-type liquid container has fallen sideways, the movable section is brought closer to the liquid-side surface of the inside plug body by gravity, and this reduces a clearance between the movable section and the liquid-side surface. Further, the liquid stored in the container body rises between the movable section and the liquid-side surface by the capillary action, so that the through hole provided on the liquid-side surface is filled with the liquid.

As such, in a case where the suction-type liquid container has fallen sideways, the inside plug in accordance with the present invention prevents leakage of the liquid from the container body by blocking, with the liquid, the through hole (i.e., air conduit) provided on the liquid-side surface, by utilizing the capillary action.

Advantageous Effects of Invention

The inside plug in accordance with the present invention includes: an inside plug body which is held at the opening; a liquid absorbent wick holding section for holding the liquid absorbent wick, the liquid absorbent wick holding section being connected to the inside plug body; and a movable section which (i) is located in an inner space of the container body in a state where the inside plug body is held at the opening and (ii) is movable in a direction along the liquid absorbent wick holding section, the inside plug body having, on a liquid-side surface thereof, a through hole through which the inner space of the container body communicates with outside air, the liquid-side surface being a surface of the inside plug body and being located on a side of the liquid stored in the container body, and the movable section being brought closer to the liquid-side surface by gravity in a case where the suction-type liquid container has fallen sideways.

This makes it possible to bring about an effect of providing an inside plug that prevents leakage of a liquid.

BRIEF DESCRIPTION OF DRAWINGS

FIG. 25 is an external view illustrating an inside plug in accordance with the present embodiment. (a) of FIG. 25 is a front view illustrating the inside plug. (b) of FIG. 25 is a bottom view illustrating the inside plug.

FIG. 26 is an external view illustrating another inside plug in accordance with the present embodiment. (a) of FIG. 25 is a front view illustrating the inside plug. (b) of FIG. 25 is a bottom view illustrating the inside plug.

DESCRIPTION OF EMBODIMENTS

Figure 1:
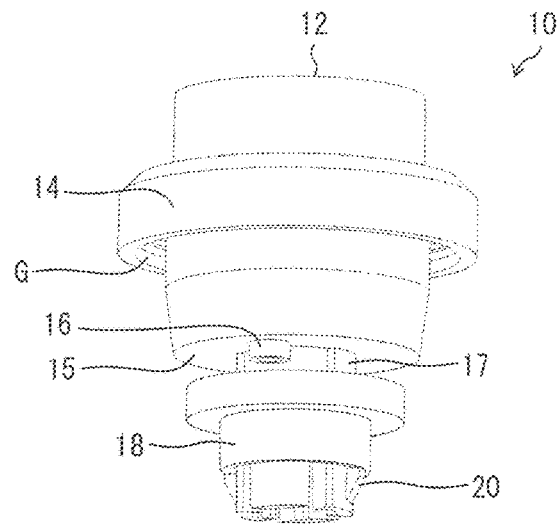
FIG. 1 is an external view illustrating an inside plug in accordance with the present embodiment.

The following description discusses, with reference to the drawings, a suction-type liquid container 1 in accordance with the present embodiment. In the following description, identical parts and components are given identical reference numerals, and have identical names and functions. Accordingly, detailed descriptions thereof are not repeated.

[Configuration of Suction-Type Liquid Container 1]

Figure 2:
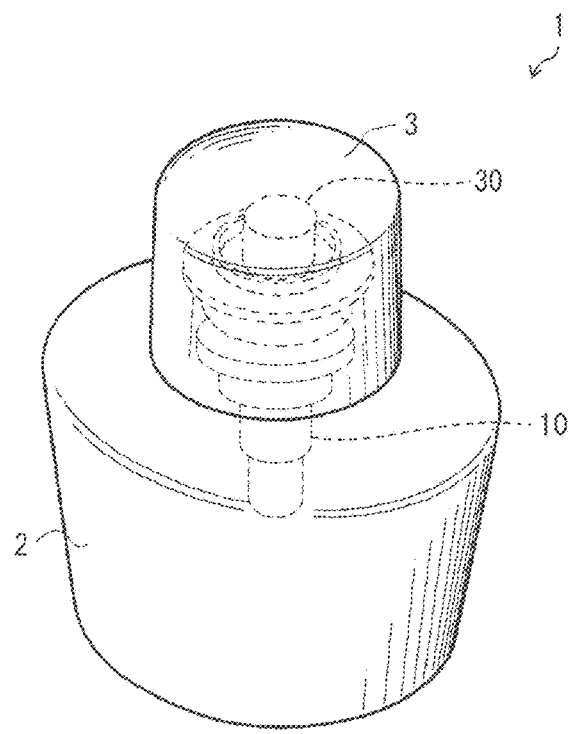
FIG. 2 is an external perspective view illustrating a suction-type liquid container in accordance with the present embodiment.

FIG. 2 is an external perspective view illustrating the suction-type liquid container 1. The suction-type liquid container 1 includes a container body 2, an outside plug 3, an inside plug 10, and a liquid absorbent wick 30. In the suction-type liquid container 1, a liquid stored in the container body 2 is sucked up by capillary action which is achieved by the liquid absorbent wick 30. The liquid thus sucked-up is then diffused to an outside of a device by being, for example, heated, evaporated, or vibrated.

According to the present embodiment, the "liquid" means a liquid having an aromatic function, a deodorizing function, or an insecticidal function, that is, the "liquid" can be an aromatic, a deodorant, an insecticide, or the like. Note, however, that the liquid is not limited to a liquid having any of the above functions. For example, the liquid can be water to be used for humidification.

The container body 2 stores therein a liquid. The container body 2 can be made of a material such as glass, plastic, or the like. The container body 2 has a cylindrical shape and has an opening which is narrower than a body part of the container body 2. The inside plug 10 holding the liquid absorbent wick 30 is attached to an inside of the opening of the container body 2. Further, the outside plug 3 is removably attached to an outside of the opening of the container body 2.

A shape of the container body 2 is not limited to the cylindrical shape and can be any of various shapes. For example, the container body 2 can (i) be freely designed in accordance with a usage, a used situation, an appearance, and the like and (ii) have a shape such as a quadrangular prism shape, a spherical shape, or a hemispherical shape. The outside plug 3 can be attached to the container body 2 by a well-known method such as twisting or fitting.

The outside plug 3 is removably attached to the opening of the container body 2 and functions as a lid. That is, the outside plug 3 can be also referred to as a cap for preventing leakage of a liquid from the container body 2. The outside plug 3 can be made of a material such as glass or plastic.

Figure 3:
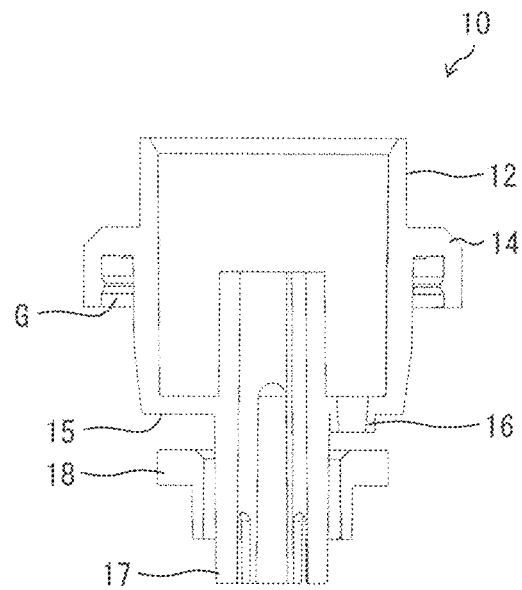
FIG. 3 is a cross sectional view illustrating the inside plug in accordance with the present embodiment.

The following description discusses the inside plug 10 with reference to FIG. 1 etc. FIG. 1 is an external view illustrating the inside plug 10. FIG. 3 is a cross sectional view illustrating the inside plug 10.

According to the present embodiment, a direction of gravity is defined as a downward direction and a direction opposite to the direction of gravity is defined as an upward direction. In FIGS. 1 and 3, lower sides of FIGS. 1 and 3 are each a direction of gravity (i.e., the downward direction), and the container body 2 (not illustrated) is located below the inside plug 10.

The inside plug 10 holds the liquid absorbent wick 30 and is attached to the opening of the container body 2. The inside plug 10 includes an inside plug body 12, a bottle plug 14, a protrusion section 16, a liquid absorbent wick holding section 17, a ring 18 (movable section), and a ring stopping section 20.

The inside plug body 12, the bottle plug 14, the protrusion section 16, the liquid absorbent wick holding section 17, and the ring stopping section 20 can be integrally formed or can be separately formed. Note, however, that, in terms of production, cost, and the like, it is preferable to integrally form the above members by injection molding by use of a plastic resin. The following description discusses a case where the inside plug body 12, the bottle plug 14, the protrusion section 16, the liquid absorbent wick holding section 17, and the ring stopping section 20 are integrally formed. In a case where the inside plug body 12, the bottle plug 14, the protrusion section 16, the liquid absorbent wick holding section 17, and the ring stopping section 20 are integrally formed, it is possible to express that the inside plug body 12 includes the bottle plug 14, the protrusion section 16, the liquid absorbent wick holding section 17, and the ring stopping section 20.

Note that the inside plug body 12, the bottle plug 14, the protrusion section 16, the liquid absorbent wick holding section 17, the ring 18, and the ring stopping section 20 are not necessarily made of plastic and can be made of a material such as metal.

The following description discusses each of the members with reference to FIGS. 1 and 3.

The inside plug body 12 has a cylindrical shape, and the cylindrical part of the inside plug body 12 is slightly smaller in diameter than the opening of the container body 2. Thus, in a case where the inside plug body 12 is fitted into the opening of the container body 2, the inside plug body 12 is brought into close contact with the opening of the container body 2. This prevents leakage of a liquid from between the container body 2 and the inside plug body 12 even in a case where the container body 2 is inverted (i.e., upside down).

The bottle plug 14 and the liquid absorbent wick holding section 17 are provided so as to be integrated with the inside plug body 12. Alternatively, it is possible to express that the bottle plug 14 and the liquid absorbent wick holding section 17 are connected to the inside plug body 12. A facing surface of the inside plug body 12, which facing surface faces the ring 18, is flat or substantially flat (i.e., a flat surface 15 illustrated in FIGS. 1 and 3). In other words, the flat surface 15 is a surface of the inside plug body 12 and is a liquid-side surface provided on a side of the liquid stored in the container body 2.

A shape of the inside plug body 12 is not limited to the cylindrical shape. The inside plug body 12 can have another shape such as a quadrangular shape or a triangular shape, provided that the inside plug body 12 is brought into close contact with the opening of the container body 2 in a case where the inside plug body 12 is fitted into the opening of the container body 2.

The inside plug body 12 is hollow and communicates with an inside of the container body 2 via a through hole which passes through the protrusion section 16 in an up-and-down direction.

The bottle plug 14 is provided so as to be integrated with the inside plug body 12, and there is a gap G between the bottle plug 14 and the inside plug body 12. In a case where the inside plug body 12 is fitted into the container body 2, an end of the opening of the container body 2 is fitted into the gap G. In this arrangement, the inside of the opening of the container body 2 is in close contact with an outer surface of the inside plug body 12, and the outside of the opening of the container body 2 and an upper end of the opening of the container body 2 are in close contact with the bottle plug 14. Thus, in a case where the container body 2 is fitted into the inside plug body 12, the inside, the upper end, and the outside of the opening of the container body 2 are in close contact with the inside plug body 12 and/or the bottle plug 14. This prevents leakage of the liquid from between the opening of the container body 2 and the inside plug body 12 even in a case where the container body 2 is held in an inverted (i.e., upside down) position.

Figure 4:
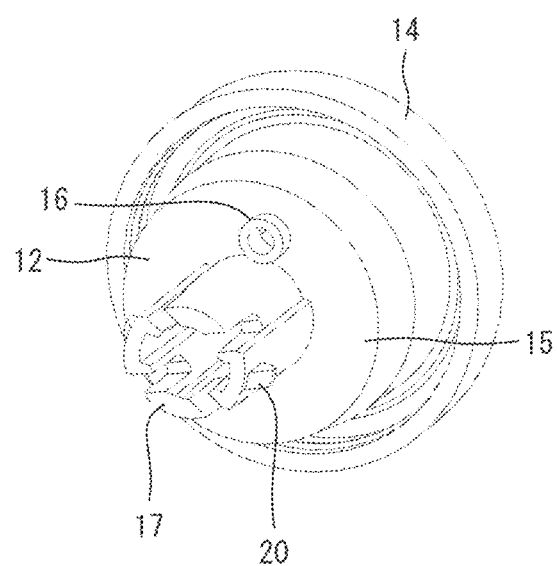
FIG. 4 is an external view illustrating the inside plug body viewed from below.

The following description discusses the protrusion section 16 with reference to FIG. 4. FIG. 4 is an external view illustrating the inside plug body 12 viewed from below.

The protrusion section 16 is provided on the flat surface (liquid-side surface) 15 located in a lower part of the inside plug body 12. In a case where the inside plug body 12 is held at the opening of the container body 2, the protrusion section 16 is located in an inner space of the container body 2. The protrusion section 16 protrudes from the flat surface 15. A through hole (see FIG. 3) extending in the up-and-down direction is provided inside of the protrusion section 16. In other words, the through hole is provided so as to pass through the flat surface 15 and the protrusion section 16.

Thus, in a case where the inside plug body 12 is fitted into the opening of the container body 2, an inside of the inside plug body 12 communicates with the inside of the container body 2 via the through hole of the protrusion section 16. The protrusion section 16 can be provided at any position on the flat surface 15.

The through hole provided in the protrusion section 16 is preferably tapered so that an upper side of the through hole is wider than a lower side of the through hole in a state where the suction-type liquid container 1 is standing (see FIG. 3). The through hole provided in the protrusion section 16 has, for example, a diameter of 2 mm on the upper side and a diameter of 1.8 mm on the lower side.

A shape of the through hole is not limited to the circular shape and can be another shape such as a quadrangular shape or a triangular shape. The protrusion section 16 has, for example, a height of 0.5 mm to 1 mm from the flat surface 15.

The protrusion section 16 has the through hole for the following reasons. That is, in a case where a liquid is diffused from the suction-type liquid container 1, an internal pressure of the container body 2 is reduced, and this makes it difficult to diffuse the liquid from the suction-type liquid container 1. In view of this, the through hole is provided in the protrusion section 16 so that the inside of the container body 2 communicates with outside air, and this allows the internal pressure of the container body 2 to be kept constant. This makes it possible to keep a stable amount of liquid to be diffused from the suction-type liquid container 1.

As illustrated in FIG. 3, the liquid absorbent wick holding section 17 is provided so as to (i) be integrated with the inside plug body 12 and (ii) be elongated from the inside of the inside plug body 12 toward the container body 2. The liquid absorbent wick holding section 17 (i) has a through hole extending in a longitudinal direction and (ii) holds, by an inner wall of the through hole or the like, the liquid absorbent wick 30 which is inserted into the through hole. This allows the liquid absorbent wick holding section 17 to hold the liquid absorbent wick 30 such that (i) one end of the liquid absorbent wick 30 is located inside the inside plug body 12 and (ii) the other end of the liquid absorbent wick 30 is located in the liquid stored in the container body 2.

The ring stopping section 20 is provided in the liquid absorbent wick holding section 17, and controls a downward movement of the ring 18 in a state where the suction-type liquid container 1 is standing. In FIG. 1, the liquid absorbent wick holding section 17 includes two ring stopping sections 20. Note, however, that the number of ring stopping sections 20 is not limited to two. Alternatively, the liquid absorbent wick holding section 17 can have one ring stopping section 20 or three or more ring stopping sections 20. Further, a shape and a structure of the ring stopping section 20 are not limited to particular ones, provided that the ring stopping section 20 controls the downward movement of the ring 18 in a state where the suction-type liquid container 1 is standing.

The liquid absorbent wick 30 (i) is inserted in the container body 2 and (ii) sucks up, from one end of the liquid absorbent wick 30 by the capillary action, the liquid stored in the container body 2. The liquid thus sucked-up is then diffused from the other end of the liquid absorbent wick 30 to the outside of the suction-type liquid container 1 by being heated, evaporated, vibrated, or the like.

The liquid absorbent wick 30 is preferably made of, for example, a porous body having continuous holes, an open-cell resin body, or a resin fiber assembly. Specific examples of materials of which the liquid absorbent wick 30 is made encompass, but not limited to: an open-cell resin body made of polyurethane, polyethylene, polyethylene terephthalate, polyvinyl formal, polystyrene, or the like; a porous body obtained by tableting and sintering, as a main component, resin fine particles of polyethylene, polypropylene, nylon, or the like; a porous body made of polyethylene fluoride or the like; a felt member made of polyester, polypropylene, nylon, acrylic, rayon, wool, or the like; a resin fiber assembly such as nonwoven fabric made of polyolefin fibers, polyester fibers, nylon fibers, rayon fibers, acrylic fibers, vinylon fibers, polychlal fibers, aramid fibers, or the like; and a porous inorganic powder sintered body obtained by tableting and sintering inorganic powder such as ceramic or the like as a main component. The specific examples of the materials further encompass the above materials treated with a surfactant.

Figure 5:
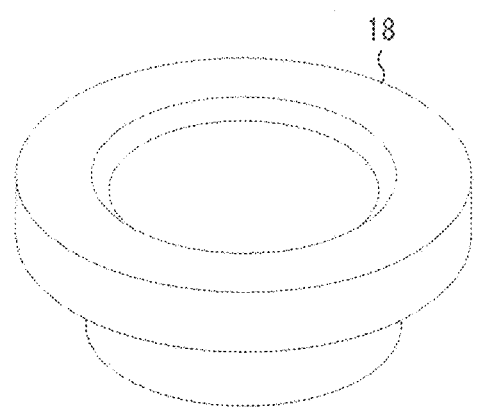
FIG. 5 is an external view illustrating a ring.

The following description discusses the ring 18 with reference to FIGS. 5 and 1. FIG. 5 is an external view illustrating the ring 18.

The ring 18 has a ring shape, and the liquid absorbent wick holding section 17 is fitted inside an inner periphery of the ring 18. In other words, the ring 18 has a ring shape surrounding the liquid absorbent wick holding section 17. The ring 18 (i) is not fixed to the liquid absorbent wick holding section 17 and (ii) moves in the longitudinal direction of the liquid absorbent wick holding section 17 in a range defined by (a) the protrusion section 16 and the flat surface 15 and (b) the ring stopping section 20. The ring 18 is loosely attached to the liquid absorbent wick holding section 17 so that the ring 18 is highly movable (slidable) with respect to the liquid absorbent wick holding section 17.

Thus, in a state in which the suction-type liquid container 1 is standing, the ring 18 moves in the downward direction by gravity, i.e., a weight of the ring 18 itself. The downward movement of the ring 18 is stopped by the ring stopping section 20. Meanwhile, in a case where the protrusion section 16 is located below the ring stopping section 20, for example, in a case where the suction-type liquid container 1 has fallen sideways, the ring 18 moves toward the flat surface 15 and the protrusion section 16 so as to come closer to the flat surface 15 and the protrusion section 16.

The term being "closer to encompasses an action of approaching an object, a state of being in contact with an object, and a state of being present extremely near an object. Accordingly, the phrase the ring 18 is brought closer to the flat surface 15 and the protrusion section 16" means, for example, that the ring 18 is in contact with the flat surface 15 and the protrusion section 16 or that the ring 18 is located extremely near the flat surface 15 and the protrusion section 16.

The ring 18 has specific gravity higher than that of the liquid stored in the container body 2. Since the ring 18 has specific gravity higher than that of the liquid stored in the container body 2, the ring 18 (i) is sunk in the liquid and (ii) allows the through hole, which is provided in the protrusion section 16, to serve as the ventilation structure.

In a case where the inside plug body 12, the bottle plug 14, the protrusion section 16, the liquid absorbent wick holding section 17, the ring 18, and the ring stopping section 20 are made of plastic materials, such plastic materials are preferably selected in the following manner. That is, the inside plug body 12, the bottle plug 14, the protrusion section 16, the liquid absorbent wick holding section 17, and the ring stopping section 20 are made of a plastic material different from that of the ring 18. This allows the ring 18 to have higher mobility and slidability with respect to the liquid absorbent wick holding section 17 and the like. For example, (i) the inside plug body 12, the bottle plug 14, the protrusion section 16, the liquid absorbent wick holding section 17, and the ring stopping section 20 are made of polypropylene and (ii) the ring 18 is made of polyacetal.

Note that, in a case where the ring 18 is made of a material different from that of the liquid absorbent wick holding section 17, it is possible to increase mobility and slidability of the ring 18 with respect to the liquid absorbent wick holding section 17. This is because molecular bonding strength (e.g., van der Waals forces etc.) is typically higher between identical materials and is smaller between different materials. The ring 18 and the liquid absorbent wick holding section 17 can be made of, for example, different kinds of materials such as metal and resin.

A thickness and a material of the ring 18 are not limited to particular ones, provided that the ring 18 serves a function described in the section [Operation of ring 18 and effect 2 thereof] (described later). Thus, the ring 18 can be made up of a thin ring-shaped member such as a washer. Moreover, the ring 18 does not necessarily have a completely-closed ring shape and can have, for example, an incomplete ring shape (i.e., a shape of a Roman alphabet "C") or the like, provided that the ring 18 serves the function described in the section [Operation of ring 18 and effect 2 thereof].

The following description discusses, in terms of relation with the ring 18, a reason that the protrusion section 16 is provided. As described above, the protrusion section 16 protrudes from the flat surface 15. In the following description, a case where the protrusion section 16 is provided on the flat surface 15 is compared with a case where the protrusion section 16 is not provided on the flat surface 15 and only a through hole is provided on the flat surface 15.

In a case where (i) the protrusion section 16 is not provided on the flat surface 15 and only the through hole is provided on the flat surface 15 and (ii) the ring 18 has once stuck to the flat surface 15, it may be difficult for the ring 18 to separate from the flat surface 15. In such a case, the through hole provided on the flat surface 15 loses a ventilation function of allowing the inside plug body 12 to communicate with the container body 2, and this may prevent a stable operation of the suction-type liquid container 1. Moreover, in such a case, a liquid accumulated in the inside plug body 12 cannot return to the container body 2. For these reasons, according to the suction-type liquid container 1, the protrusion section 16 is provided on the flat surface 15 so that the ring 18 easily separates from the flat surface 15.

Note, however, that the flat surface 15 does not necessarily need to have the protrusion section 16. This is because, by causing the flat surface 15 to have slight roughness, it is possible to facilitate separation between the flat surface 15 and the ring 18. In a case where the flat surface 15 does not have the protrusion section 16, the through hole of the protrusion section 16 can be substituted by a configuration provided on the flat surface 15.

Figure 6:
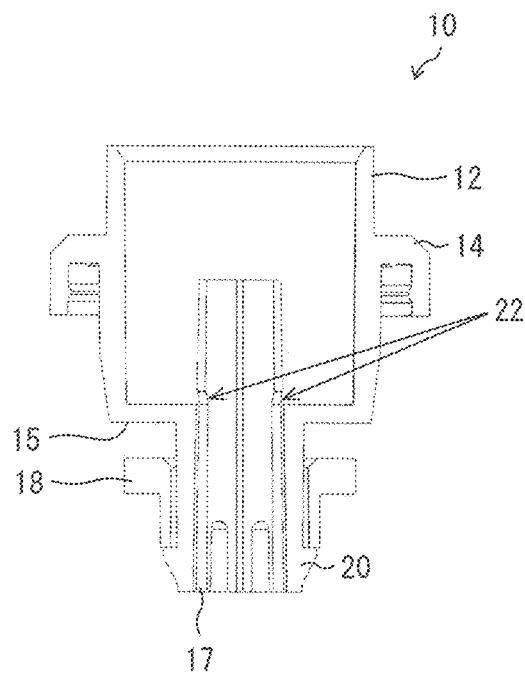
FIG. 6 is a cross sectional view illustrating the inside plug in accordance with the present embodiment.

The following description discusses, with reference to FIG. 6, a liquid discharge hole 22 provided in the liquid absorbent wick holding section 17. FIG. 6 is a cross sectional view illustrating the inside plug 10. Note that FIG. 6 illustrates a cross section which (i) is perpendicular to a line segment connecting (a) a center of the liquid absorbent wick holding section 17 and (b) the protrusion section 16 and (ii) passes through the center of the liquid absorbent wick holding section 17.

As illustrated in FIG. 6, two liquid discharge holes 22 are provided in the liquid absorbent wick holding section 17. The two liquid discharge holes 22 are provided (i) on a wall surface of the liquid absorbent wick holding section 17 which wall surface is located near a bottom surface part of the inside plug body 12 which is hollow and (ii) at positions facing each other. The liquid discharge holes 22 are provided in the liquid absorbent wick holding section 17 for the following reasons.

The following description discusses a case where the suction-type liquid container 1 has fallen sideways. In such a case, the liquid stored in the container body 2 is sucked up by the liquid absorbent wick 30, and the liquid thus sucked up may leak from the container body 2. In view of this, by the presence of the liquid discharge holes 22, the liquid absorbed by the liquid absorbent wick 30 is discharged to the inside plug body 12 via the liquid discharge holes 22 and is then accumulated in the inside plug body 12. The liquid accumulated in the inside plug body 12 passes through the through hole of the protrusion section 16 and thus returns to the container body 2. In this manner, even in a case where the suction-type liquid container 1 has fallen sideways, the liquid discharge holes 22 provided in the liquid absorbent wick holding section 17 make it possible to prevent leakage of the liquid to the outside of the suction-type liquid container 1.

In particular, in a case where a large amount of liquid is diffused from the suction-type liquid container 1, it is necessary to increase a speed at which the liquid absorbent wick 30 absorbs the liquid by the capillary action, and therefore the liquid absorbent wick 30 is configured to have high porosity. In this case, when the suction-type liquid container 1 has fallen sideways, a problem is easily caused which is leakage of a liquid via the liquid absorbent wick 30. In view of this, the liquid discharge holes 22 are provided in the liquid absorbent wick holding section 17, and this makes it possible to (i) prevent leakage of the liquid from the suction-type liquid container 1 and (ii) cause the liquid which has leaked from the container body 2 to promptly return into the container body 2.

Note that the number of liquid discharge holes 22 provided in the liquid absorbent wick holding section 17 is not limited to two and can be one or three or more. Moreover, the positions of the liquid discharge holes 22 provided in the liquid absorbent wick holding section 17 are not necessarily the positions facing each other and can be determined as appropriate. A diameter of each of the liquid discharge holes 22 can be approximately 0.5 mm to 1 mm. Each of the liquid discharge holes 22 does not need to have a circular shape and can be determined as appropriate to have another shape such as a quadrangular shape or a triangular shape.

[Operation of Ring 18 and Effect 1 Thereof]

Figure 7:
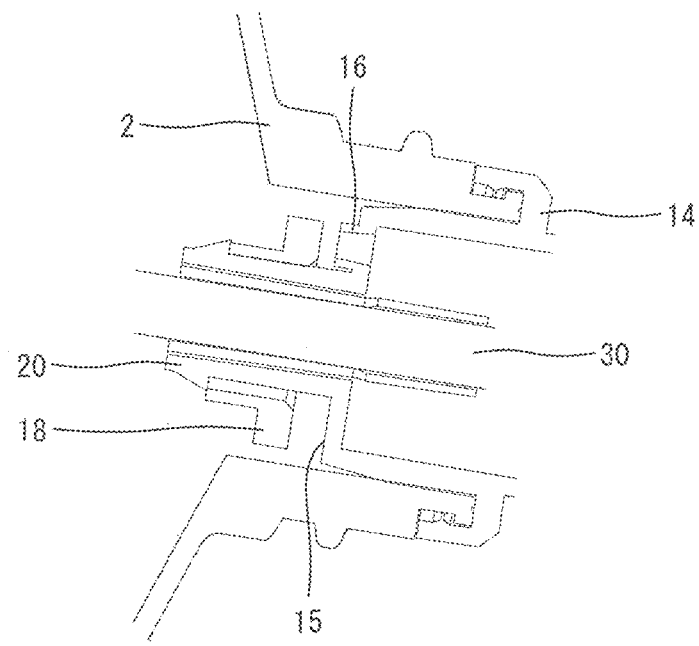
FIG. 7 is a view illustrating a position of the ring immediately after the suction-type liquid container in accordance with the present embodiment has fallen sideways while a protrusion section is located above a liquid absorbent wick.
Figure 8:
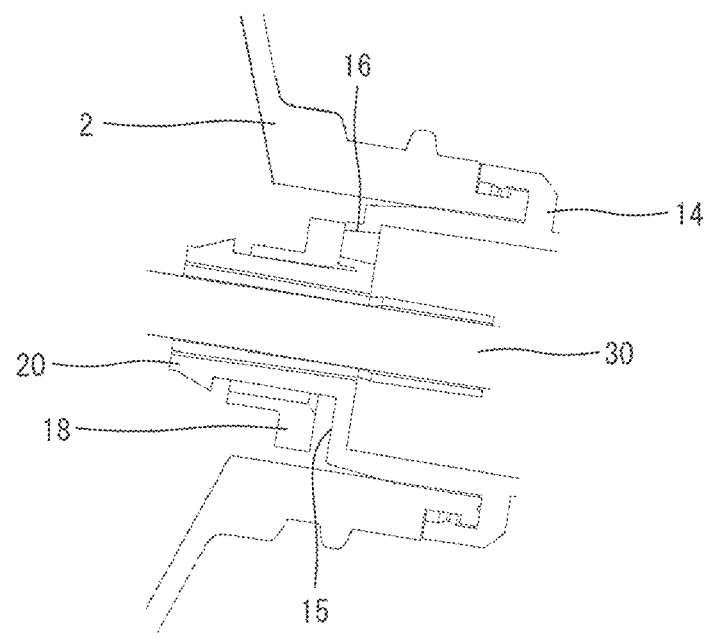
FIG. 8 is a view illustrating a position of the ring at a given time point after the suction-type liquid container in accordance with the present embodiment has fallen sideways while the protrusion section is located above the liquid absorbent wick.

The following description discusses, with reference to FIG. 7 etc., an operation of the ring 18 in a case where the suction-type liquid container 1 has fallen sideways. FIG. 7 is a view illustrating a position of the ring 18 immediately after the suction-type liquid container 1 has fallen sideways while the protrusion section 16 is located above the liquid absorbent wick 30. FIG. 8 is a view illustrating a position of the ring 18 at a given time point after the suction-type liquid container 1 has fallen sideways while the protrusion section 16 is located above the liquid absorbent wick 30.

As illustrated in FIG. 7, immediately after the suction-type liquid container 1 has fallen sideways, the ring 18 is away from the protrusion section 16.

However, at a given time point after the suction-type liquid container 1 has fallen sideways, the ring 18 moves toward the protrusion section 16 by gravity and then makes contact with the protrusion section 16 (see FIG. 8). In this case, in FIG. 8, the ring 18 is in contact with the protrusion section 16 so as to block the through hole provided in the protrusion section 16. This allows the suction-type liquid container 1 to prevent leakage of a liquid via the through hole provided in the protrusion section 16.

Figure 9:
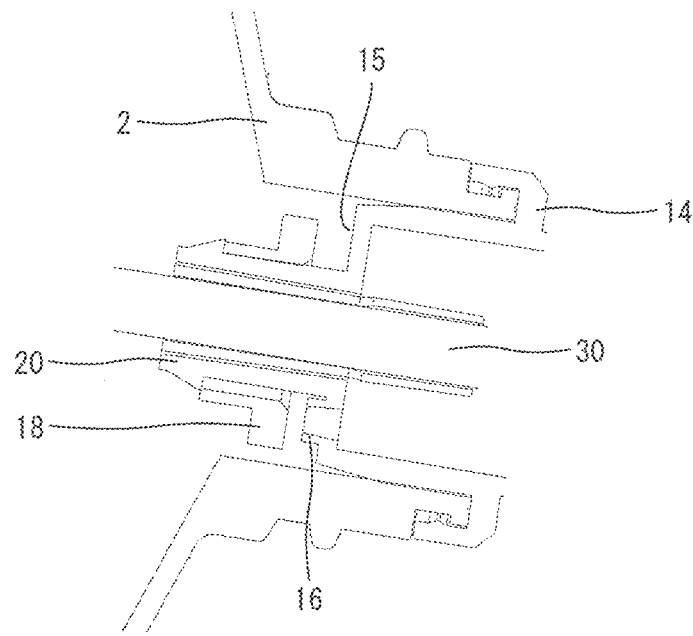
FIG. 9 is a view illustrating a position of the ring immediately after the suction-type liquid container in accordance with the present embodiment has fallen sideways while the protrusion section is located below the liquid absorbent wick.
Figure 10:
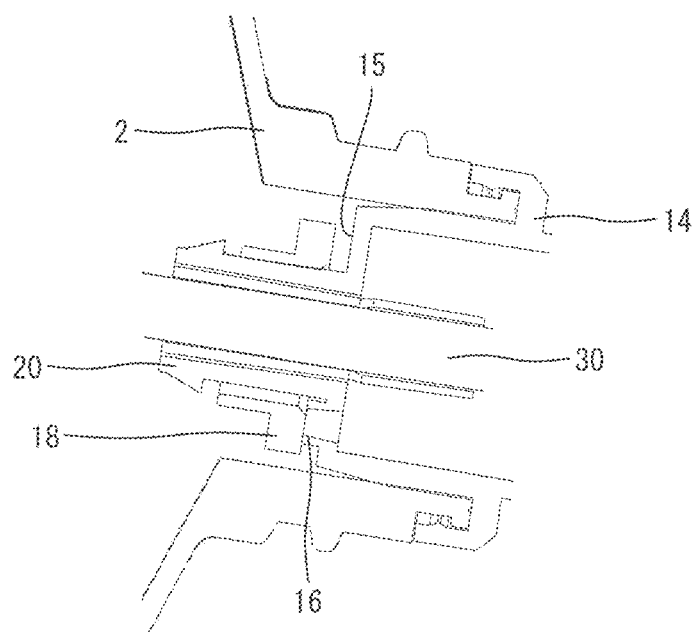
FIG. 10 is a view illustrating a position of the ring at a given time point after the suction-type liquid container in accordance with the present embodiment has fallen sideways while the protrusion section is located below the liquid absorbent wick.

The following description discusses, with reference to FIGS. 9 and 10, a case where the protrusion section 16 is located below the liquid absorbent wick 30 when the suction-type liquid container 1 has fallen sideways. FIG. 9 is a view illustrating a position of the ring 18 immediately after the suction-type liquid container 1 has fallen sideways while the protrusion section 16 is located below the liquid absorbent wick 30. FIG. 10 is a view illustrating a position of the ring 18 at a given time point after the suction-type liquid container 1 has fallen sideways while the protrusion section 16 is located below the liquid absorbent wick 30.

As illustrated in FIG. 9, immediately after the suction-type liquid container 1 has fallen sideways, the ring 18 is away from the protrusion section 16.

However, at a given time point after the suction-type liquid container 1 has fallen sideways, the ring 18 moves toward the protrusion section 16 by gravity and then makes contact with the protrusion section 16 (see FIG. 10). In this case, in FIG. 10, the ring 18 is in contact with the protrusion section 16 so as to block the through hole provided in the protrusion section 16. This allows the suction-type liquid container 1 to prevent leakage of a liquid via the through hole provided in the protrusion section 16.

As described above, in a case where the ring 18 blocks the through hole provided in the protrusion section 16, the suction-type liquid container 1 can prevent leakage of the liquid via the through hole provided in the protrusion section 16.

Note, however, that, depending on (i) a manner in which the ring 18 is in contact with the protrusion section 16 and/or (ii) a residual amount of liquid stored in the container body 2, the ring 18 may not block the through hole provided in the protrusion section 16. In view of this, the following description discusses, in sections [Relationship between gas-liquid exchange and leakage of liquid] and [Operation of ring 18 and effect 2 thereof], a principle on which the suction-type liquid container 1 prevents leakage of the liquid via the through hole provided in the protrusion section 16 in a state in which the ring 18 is not completely blocking the through hole provided in the protrusion section 16.

[Relationship Between Gas-Liquid Exchange and Leakage of Liquid]

Figure 11:
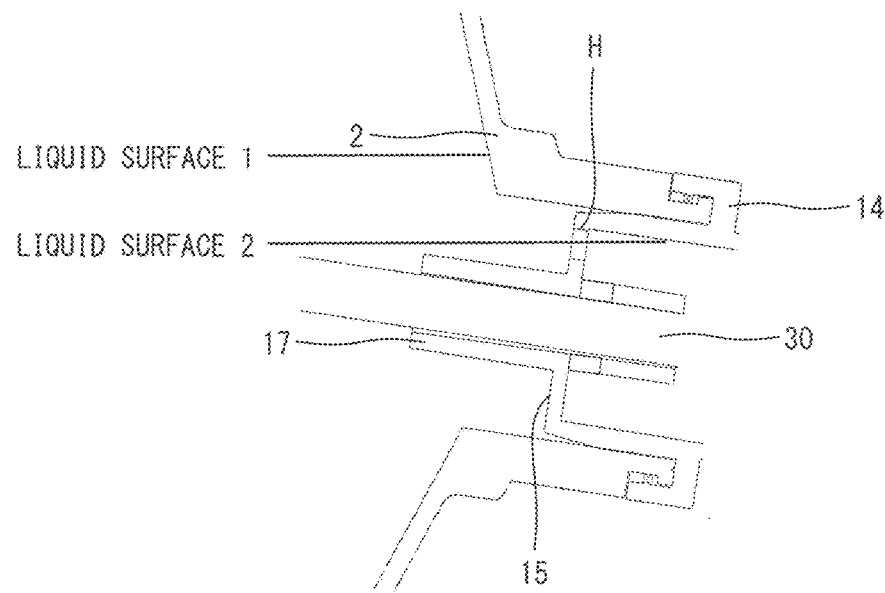
FIG. 11 is a view for explaining a relationship between (i) liquid surface levels (liquid surface 1, liquid surface 2) and (ii) leakage of a liquid via a through hole.

The following description discusses, with reference to FIG. 11, a state in which the liquid stored in the container body 2 passes through the through hole and leaks out of the container body, on the basis of a relationship between a liquid surface level in the container body 2 and leakage of the liquid.

FIG. 11 is a view for explaining a relationship between (i) liquid surface levels (liquid surface 1, liquid surface 2) and (ii) leakage of a liquid via a through hole H. Note that FIG. 11 illustrates a case where the through hole H is located above the liquid absorbent wick 30 when the suction-type liquid container 1 has fallen sideways. For convenience, the ring 18 is not illustrated in FIG. 11. In FIG. 11, for convenience, the through hole H is directly provided on the flat surface 15.

As illustrated in FIG. 11, the liquid surface 1 is located above the through hole H. That is, the through hole H is filled with a liquid. In this case, gas-liquid exchange hardly occurs via the through hole H. Specifically, according to a state of the liquid surface 1 illustrated in FIG. 11, the through hole H is filled with the liquid. Therefore, air is less likely to flow from the inside plug body 12 to the container body 2, and this makes it difficult for the liquid to flow from the container body 2 to the inside plug body 12.

The following description discusses a case of the liquid surface 2. The through hole H is located at a same height as the liquid surface 2 and is not completely filled with the liquid. In this case, gas-liquid exchange easily occurs via the through hole H. Specifically, according to a state of the liquid surface 2 illustrated in FIG. 11, the through hole H is not filled with the liquid. Therefore, air is more likely to flow from the inside plug body 12 to the container body 2, and this makes it easy for the liquid to flow from the container body 2 to the inside plug body 12.

That is, in a case where air flows from the inside plug body 12 to the container body 2, the liquid easily flows from the container body 2 toward the inside plug body 12. Conversely, leakage of a liquid from the container body 2 to the inside plug body 12 can be prevented merely by preventing airflow from the container body 2 to the inside plug body 12. Therefore, it is possible to prevent leakage of the liquid from the container body 2 by causing the liquid surface level of the liquid stored in the container body 2 to be located above the through hole H, like the liquid surface 1 illustrated in FIG. 11.

Figure 12:
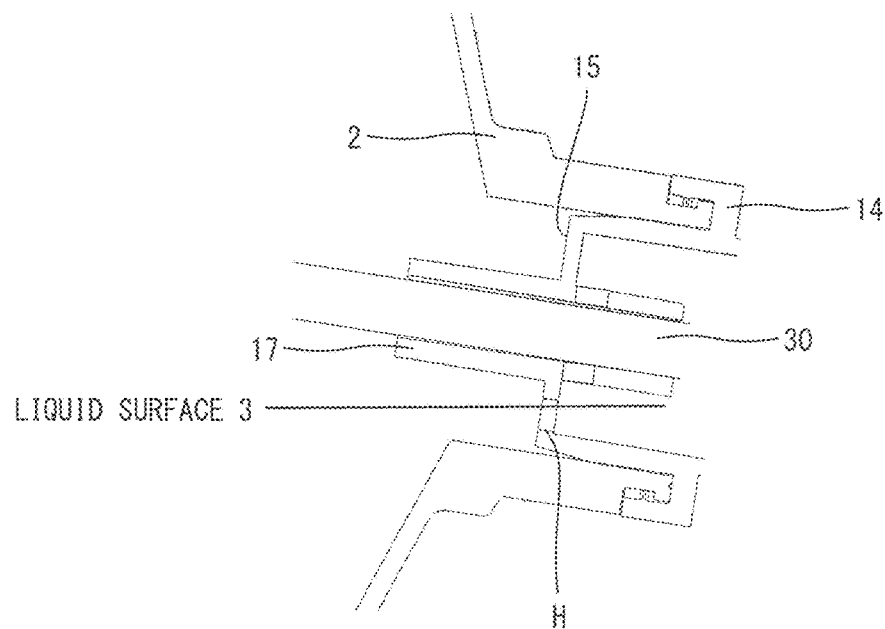
FIG. 12 is a view for explaining a relationship between a liquid surface level (liquid surface 3) and leakage of a liquid via the through hole.

The following description discusses, with reference to FIG. 12, a case which is different from that illustrated in FIG. 11. FIG. 12 is a view for explaining a relationship between a liquid surface level (liquid surface 3) and leakage of a liquid via the through hole H. Note that FIG. 12 illustrates a case where the through hole H is located below the liquid absorbent wick 30 when the suction-type liquid container 1 has fallen sideways. For convenience, the ring 18 is not illustrated in FIG. 12. In FIG. 12, for convenience, the through hole H is directly provided on the flat surface 15.

As illustrated in FIG. 12, the liquid surface 3 is located at a same height as the through hole H and is not completely filled with the liquid. In this case, gas-liquid exchange easily occurs via the through hole H. In a case where the through hole H is located below the liquid absorbent wick 30, air may enter the container body 2 via a gap between the liquid absorbent wick 30 and the liquid absorbent wick holding section 17 or the like and therefore leakage of the liquid may occur. Note, however, that, also in such a case, the ring 18 is brought closer to the flat surface 15, and this causes the liquid surface between the flat surface 15 and the ring 18 to rise. With this arrangement, leakage of the liquid via the through hole H can be prevented.

[Operation of Ring 18 and Effect 2 Thereof]

The section [Operation of ring 18 and effect 1 thereof] has discussed that, after the suction-type liquid container 1 has fallen sideways, the ring 18 blocks the through hole provided in the protrusion section 16 and thus prevents leakage of the liquid from the container body 2.

Note, however, that there is a case where the ring 18 cannot completely block the through hole provided in the protrusion section 16 after the suction-type liquid container 1 has fallen sideways. Even in such a case, the suction-type liquid container 1 can prevent leakage of the liquid from the container body 2 by a method described below with reference to FIG. 13 and the like.

Figure 13:
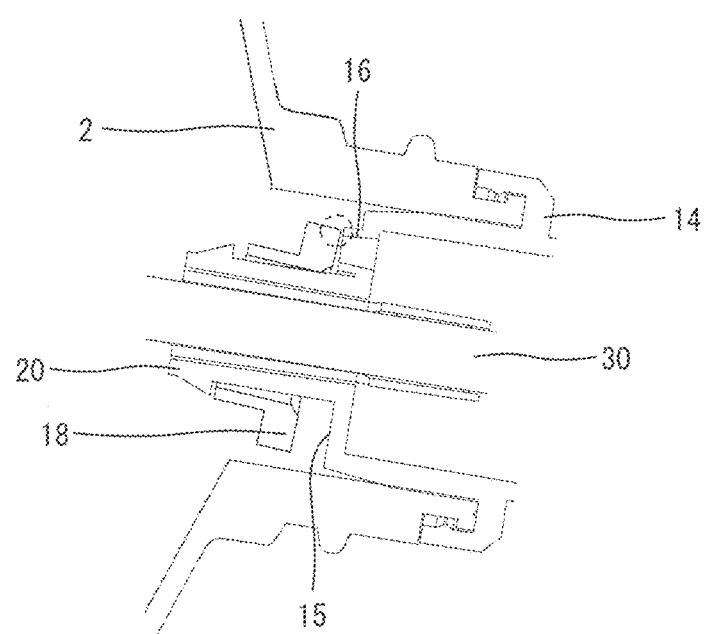
FIG. 13 is a view illustrating a state in which the ring has fallen toward the protrusion section while the protrusion section is located above the liquid absorbent wick.

FIG. 13 is a view illustrating a state in which the ring 18 has fallen toward the protrusion section 16 while the protrusion section 16 is located above the liquid absorbent wick 30.

According to the example illustrated in FIG. 13, after the suction-type liquid container 1 has fallen sideways, the ring 18 does not completely block the through hole provided in the protrusion section 16. Therefore, it is expected that gas-liquid exchange which occurs via the through hole of the protrusion section 16 causes leakage of the liquid from the container body 2 via the through hole provided in the protrusion section 16.

Note, however, that the ring 18 is brought closer to the protrusion section 16 by gravity. Therefore, a liquid rises between the flat surface 15 and the ring 18 by the capillary action, and this causes a liquid film to be formed at a position indicated by a broken line in FIG. 13. That is, the position at which the liquid film is located is a liquid surface level of the liquid existing between the flat surface 15 and the ring 18.

This causes the through hole of the protrusion section 16 to be filled with the liquid, and gas-liquid exchange hardly occurs via the through hole of the protrusion section 16. This makes it possible to prevent leakage of the liquid from the container body 2.

Figure 14:
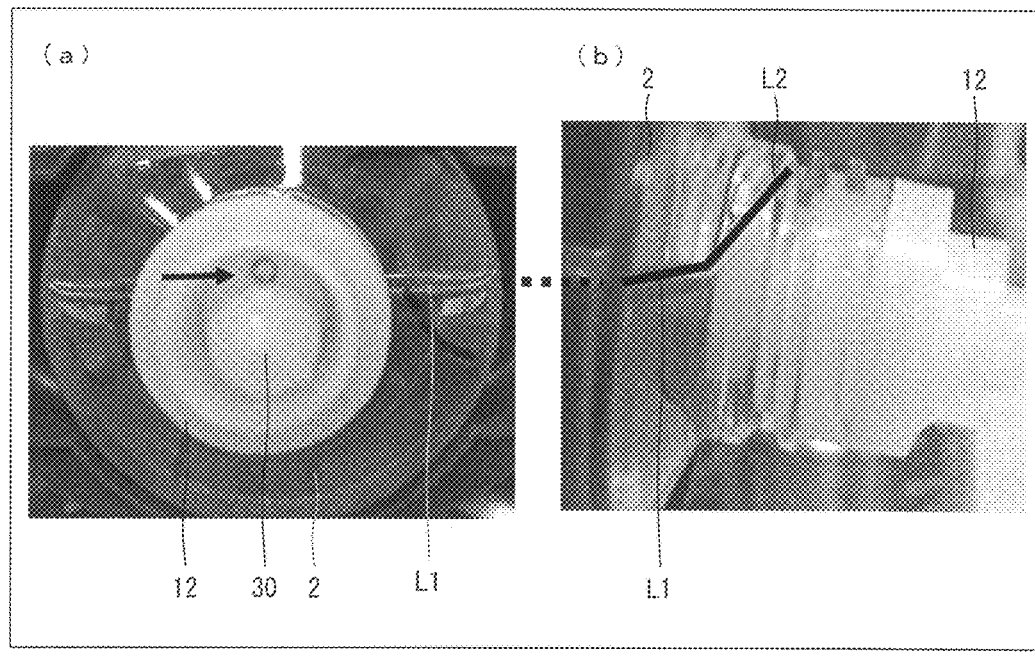
FIG. 14 is a photograph showing a liquid surface level in a case where the ring has been brought closer to a flat surface. (a) of FIG. 14 is a photograph showing a liquid surface level in the suction-type liquid container viewed from a side of an opening of the container body in a state where the suction-type liquid container has fallen sideways. (b) of FIG. 14 is a photograph showing a liquid surface level at the opening of the container body in a state where the suction-type liquid container has fallen sideways.

FIG. 14 is a photograph showing a liquid surface level in a case where the ring 18 has been brought closer to the flat surface 15. (a) of FIG. 14 is a photograph showing a liquid surface level in the suction-type liquid container 1 viewed from a side of the opening of the container body 2 in a state where the suction-type liquid container 1 has fallen sideways. (b) of FIG. 14 is a photograph showing a liquid surface level at the opening of the container body 2 in a state where the suction-type liquid container 1 has fallen sideways.

An arrow shown in (a) of FIG. 14 indicates the through hole of the protrusion section 16. As shown in (a) of FIG. 14, a liquid surface (i.e., L1 shown in (a) of FIG. 14) of a liquid stored in the container body is located lower than a position of the through hole of the protrusion section 16.

As shown in (b) of FIG. 14, however, at the opening of the container body 2, the liquid surface level changes from L1 to L2, which is located above the through hole of the protrusion section 16. This is because, in a case where the ring 18 has been brought closer to the flat surface 15, the liquid rises between the flat surface 15 and the ring 18 by the capillary action. As a result, at the opening of the container body 2, the liquid surface level rises from L1 to L2. Consequently, as described above, this allows the suction-type liquid container 1 to prevent leakage of the liquid from the container body 2 to the inside plug body 12.

Figure 15:
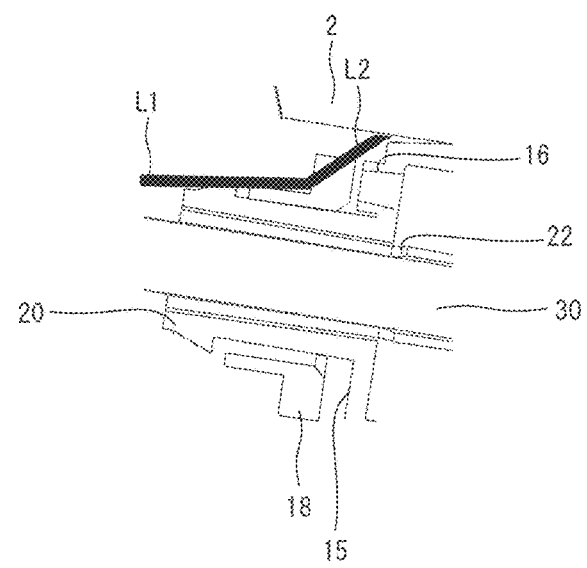
FIG. 15 is a view for simply explaining a state shown in (b) of FIG. 14.

FIG. 15 is a view for simply explaining the state shown in (b) of FIG. 14. As illustrated in FIG. 15, in a case where the ring 18 has been brought closer to the flat surface 15, the capillary action occurs between the flat surface 15 and the ring 18, so that the liquid surface level rises from L1 to L2. This causes the through hole of the protrusion section 16 to be filled with the liquid. In a case where the through hole of the protrusion section 16 is filled with the liquid, gas-liquid exchange hardly occurs via the through hole of the protrusion section 16. This consequently prevents leakage of the liquid from the container body 2 to the inside plug body 12. This effect of preventing leakage of the liquid is particularly effective in a case where a liquid surface level is equal to that of the liquid surface 2 illustrated in FIG. 11 (i.e., a case where the liquid surface level is at a position of the through hole of the protrusion section 16).

Figure 16:
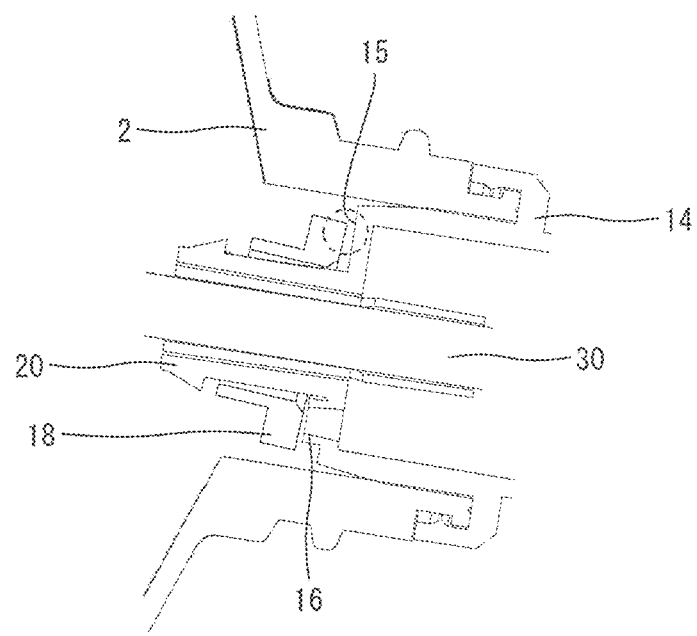
FIG. 16 is a view illustrating a state in which the ring has fallen toward the protrusion section while the protrusion section is located below the liquid absorbent wick.

FIG. 16 is a view illustrating a state in which the ring 18 has fallen toward the protrusion section 16 while the protrusion section 16 is located below the liquid absorbent wick 30.

Also in this case, due to the reasons discussed with reference to FIGS. 13 through 15, the capillary action which is caused in a case where the ring 18 has been brought closer to the flat surface 15 prevents leakage of the liquid from the container body 2.

Figure 17:
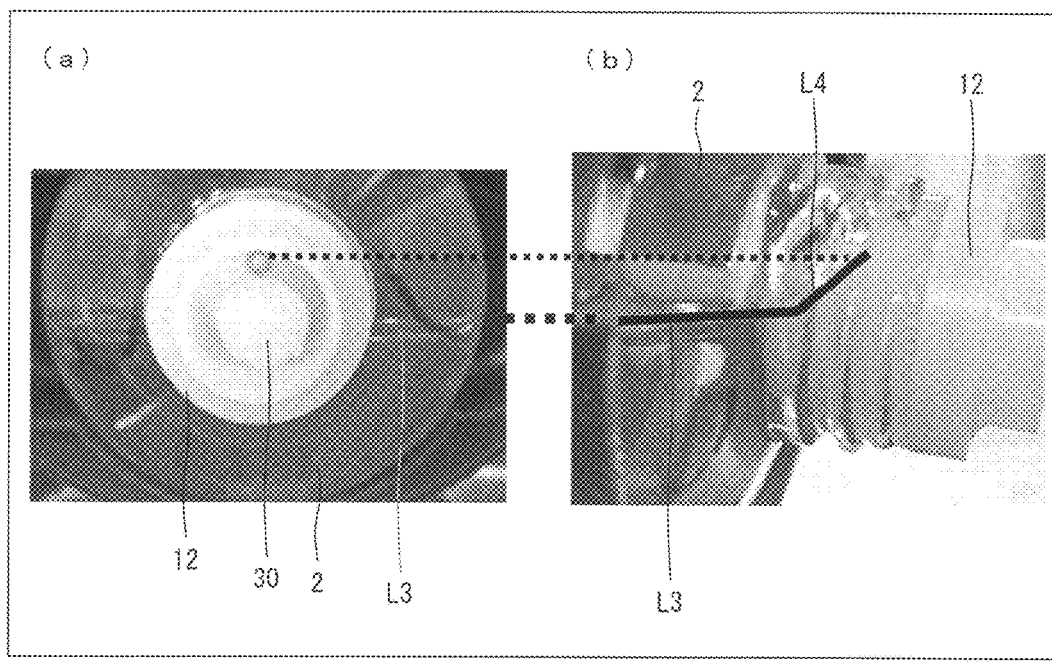
FIG. 17 is a photograph showing a liquid surface level in a case where the suction-type liquid container does not include a ring. (a) of FIG. 17 is a photograph showing a liquid surface level in the suction-type liquid container viewed from a side of an opening of the container body in a state where the suction-type liquid container has fallen sideways. (b) of FIG. 17 is a photograph showing a liquid surface level at the opening of the container body in a state where the suction-type liquid container has fallen sideways.
Figure 18:
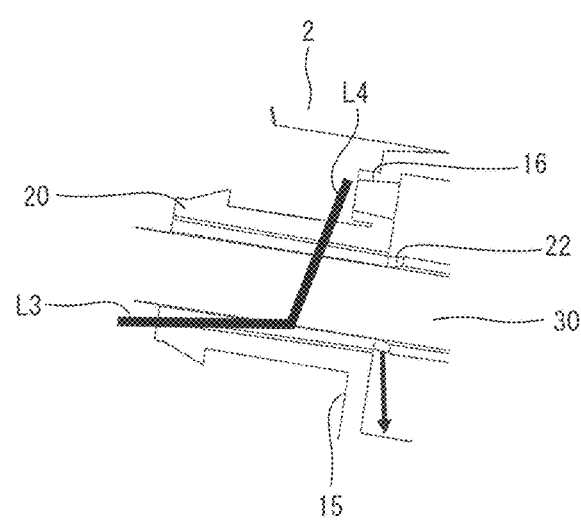
FIG. 18 is a view for simply explaining a state shown in (b) of FIG. 17.

The following description discusses leakage of the liquid caused in a case where the suction-type liquid container 1 does not include a ring, with reference to FIGS. 17 and 18 as comparative examples of the cases illustrated in FIGS. 14 and 15, respectively.

FIG. 17 is a photograph showing a liquid surface level in a case where the suction-type liquid container 1 does not include the ring 18. (a) of FIG. 17 is a photograph showing a liquid surface level in the suction-type liquid container 1 viewed from the side of the opening of the container body 2 in a state where the suction-type liquid container 1 has fallen sideways. (b) of FIG. 17 is a photograph showing a liquid surface level at the opening of the container body 2 in a state where the suction-type liquid container 1 has fallen sideways. FIG. 18 is a view for simply explaining a state shown in (b) of FIG. 17.

In FIG. 17, the suction-type liquid container does not include the ring 18. Therefore, although a liquid surface level of a liquid surface L3 rises from L3 to L4 by a surface tension (see (b) of FIG. 17), the liquid surface L4 is not high enough to block the through hole of the protrusion section 16. In this case, the through hole of the protrusion section 16 is not filled with the liquid. In the case where the through hole of the protrusion section 16 is not filled with the liquid, gas-liquid exchange via the through hole of the protrusion section 16 is more likely to occur. This easily causes leakage of the liquid from the container body 2 to the inside plug body 12.

As described above, in a case where the ring 18 has fallen toward, i.e., brought closer to the flat surface 15, the suction-type liquid container 1 prevents leakage of the liquid from occurring via the through hole of the protrusion section 16 by the capillary action which is caused between the flat surface 15 and the ring 18. This means that it is unnecessary to design in detail the suction-type liquid container 1 so that the ring 18 completely blocks the through hole of the protrusion section 16 in a case where the suction-type liquid container 1 has fallen sideways. Also in regard to this point, (i) the inside plug body 12 and (ii) the suction-type liquid container 1 including the inside plug body 12 facilitate a simplification of design.

The suction-type liquid container 1 can store therein any of various liquids different in liquid characteristic, i.e., a liquid such as an aromatic, a deodorant, an insecticide, or water. In regard to this, the suction-type liquid container 1 employs the ring 18 which is movable and can be brought closer to the flat surface 15, and therefore the suction-type liquid container 1 can effectively prevent leakage of the liquid even in a case where a liquid characteristic, such as viscosity, of the liquid changes.

As such, the suction-type liquid container 1 in accordance with the present embodiment (i) is based on a technique utilizing natural phenomena such as the surface tension and the capillary action and (ii) is not based on a technique taking into consideration only force of gravity. A distance between the flat surface 15 and the ring 18 is a very important factor for the surface tension and the capillary action which play important roles for the suction-type liquid container 1 to stably operate. In regard to this, the suction-type liquid container 1 provides a mechanism for preventing leakage of the liquid by utilizing the capillary action which is caused by bringing the ring 18 closer to the flat surface 15.

[Ring 40]
[Projection Section 41 (First Projection Section)]

Figure 19:
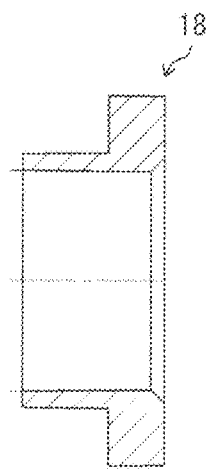
FIG. 19 is a cross sectional view illustrating a ring in accordance with the present embodiment.
Figure 20:
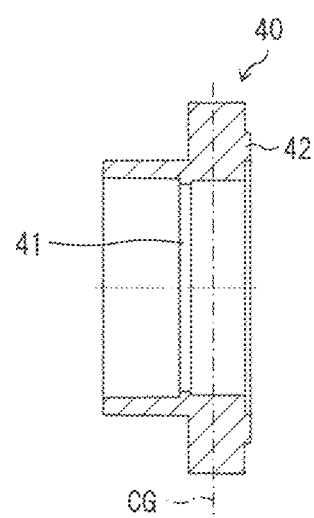
FIG. 20 is a cross sectional view illustrating another ring in accordance the present embodiment.

The following description discusses, based on comparison with the ring 18, another ring 40 which differs from the ring 18. FIG. 19 is a cross sectional view illustrating the ring 18. FIG. 20 is a cross sectional view illustrating the ring 40.

The ring 18 is a cylindrical body, and the liquid absorbent wick holding section 17 is fitted into the cylindrical body. The ring 18 (i) is not fixed to the liquid absorbent wick holding section 17 and (ii) is movable in the longitudinal direction of the liquid absorbent wick holding section 17 in a range defined by (a) the protrusion section 16 and the flat surface 15 and (b) the ring stopping section 20. The ring 18 is loosely attached to the liquid absorbent wick holding section 17 so that the ring 18 is highly movable (slidable) with respect to the liquid absorbent wick holding section 17.

Note that the cylindrical body means a shape which is hollow, like a tube or a pipe. Moreover, a shape of a cross section of an inner space of the cylindrical body is not limited to a particular one and may be any of various shapes such as a circular shape, a quadrangular shape, and a triangular shape. The cylindrical body has a given length (width) in a direction in which a hollow extends (i.e., the longitudinal direction of the liquid absorbent wick holding section 17 illustrated in FIG. 18). Further, the cylindrical body has a ring shape.

The following description discusses a case where the ring 18, the ring 40 (described later), and a ring 50 (described later) each have a cylindrical body. Further, in the following description, a surface of the ring 18 which surface faces the liquid absorbent wick holding section 17 is referred to as an inner peripheral surface of the ring 18.

The inner peripheral surface of the ring 18 is flat. Specifically, a projection section, a groove, or the like is not provided on the inner peripheral surface of the ring 18. Therefore, in a case where the ring 18 moves in the longitudinal direction of the liquid absorbent wick holding section 17, the inner peripheral surface of the ring 18 entirely makes contact with the liquid absorbent wick holding section 17.

The following description discusses the ring 40. Note that descriptions identical to those of the ring 18 are not repeated.

As illustrated in FIG. 20, the ring 40 has a projection section 41 projecting on an inner peripheral surface of the ring 40. The projection section 41 projects toward the liquid absorbent wick holding section 17. The projection section 41 is provided so as to surround the liquid absorbent wick holding section 17 throughout an entire circumference of the inner peripheral surface of the ring 40.

The ring 40 is loosely attached to the liquid absorbent wick holding section 17 so that the ring 40 is highly slidable with respect to the liquid absorbent wick holding section 17. A height of the projection section 41 can be determined as appropriate in accordance with a distance between the inner peripheral surface of the ring 40 and the liquid absorbent wick holding section 17 so that the ring 40 can keep slidability thereof with respect to the liquid absorbent wick holding section 17. The projection section 41 has a sufficiently short width in the longitudinal direction of the liquid absorbent wick holding section 17, as compared with a width of the inner peripheral surface of the ring 40 in the longitudinal direction of the liquid absorbent wick holding section 17.

The inner peripheral surface of the ring 40 is substantially flat except for the projection section 41, and the projection section 41 is provided so as to be integrated with the inner peripheral surface. Note, however, that the projection section 41 is not limited to this configuration.

The projection section "projecting on an inner peripheral surface" indicates that the projection section projects from the inner peripheral surface. In other words, "projecting on the inner peripheral surface" means that the projection section projects toward the liquid absorbent wick holding section 17 over a line connecting a first end and a second end, where (i) the first end is one end of the inner peripheral surface in the longitudinal direction of the liquid absorbent wick holding section 17 and (ii) the second end is the other end of the inner peripheral surface in the longitudinal direction of the liquid absorbent wick holding section 17. The same applies to a peak 51a described in a section [Ring 50] (later described).

The following description discusses an effect which is brought about by a feature that the ring 40 has the projection section 41 projecting on the inner peripheral surface of the ring 40.

The following description first discusses the ring 18. The ring 18 does not have the projection section 41 and makes contact with the liquid absorbent wick holding section 17 so that the inner peripheral surface itself of the ring 18 serves as a contact surface.

Meanwhile, with regard to the ring 40, the projection section 41 projecting on the inner peripheral surface of the ring 40 makes contact with the liquid absorbent wick holding section 17. Therefore, in a case where the ring 40 moves toward the through hole of the protrusion section 16, it is possible for the ring 40 to have a smaller contact area with the liquid absorbent wick holding section 17, as compared with the ring 18.

This reduces a sliding resistance between the ring 40 and the liquid absorbent wick holding section 17. Therefore, in a case where the suction-type liquid container 1 has fallen sideways, the ring 40 is more likely to be brought closer to the through hole of the protrusion section 16. As a result, as compared with the ring 18, the ring 40 can further prevent leakage of the liquid to an outside of the container body 2.

Figure 21:
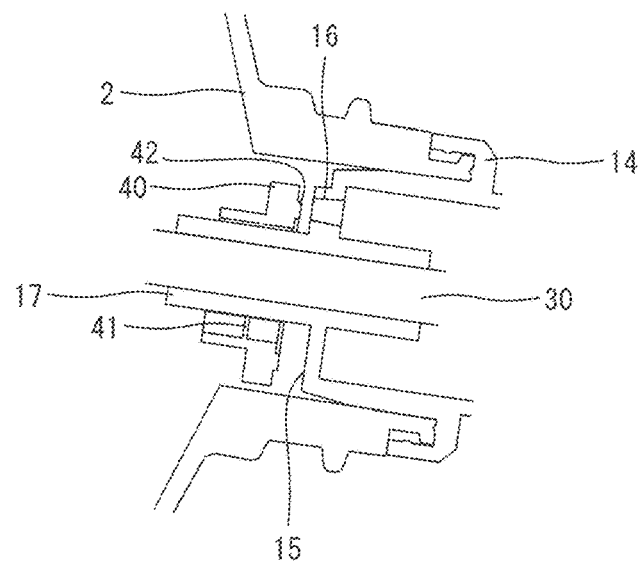
FIG. 21 is a view illustrating the ring immediately after the suction-type liquid container in accordance with the present embodiment has fallen sideways.
Figure 22:
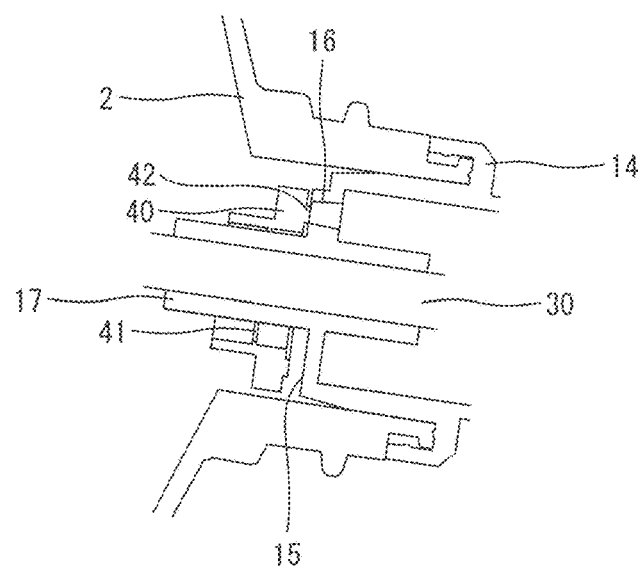
FIG. 22 is a view illustrating the ring at a time point slightly after the state illustrated in FIG. 21 occurs.

Each of FIGS. 21 and 22 is a view for explaining an operation of the ring 40 in a case where the suction-type liquid container 1 has fallen sideways. FIG. 21 is a view illustrating the ring 40 immediately after the suction-type liquid container 1 has fallen sideways. FIG. 22 is a view illustrating the ring 40 at a time point slightly after the state illustrated in FIG. 21 occurs.

As described above, the ring 18 makes contact with the liquid absorbent wick holding section 17 so that the inner peripheral surface of the ring 18 entirely makes contact with the liquid absorbent wick holding section 17. Meanwhile, with regard to the ring 40, the projection section 41 projecting from the inner peripheral surface of the ring 40 makes contact with the liquid absorbent wick holding section 17. Therefore, a sliding resistance between the ring 40 and the liquid absorbent wick holding section 17 is smaller than the sliding resistance between the ring 18 and the liquid absorbent wick holding section 17. From this, in a case where the suction-type liquid container 1 has fallen sideways, the ring 40 can be brought closer to the protrusion section 16 faster than the ring 18. As a result, use of the ring 40 makes it possible to further prevent leakage of the liquid via the through hole provided in the protrusion section 16.

Note that, as the width of the projection section 41 in the longitudinal direction of the liquid absorbent wick holding section 17 becomes smaller relative to the width of the inner peripheral surface of the ring 40 in the longitudinal direction of the liquid absorbent wick holding section 17, the sliding resistance becomes smaller between the ring 40 and the liquid absorbent wick holding section 17.

The projection section 41 can be continuously provided throughout the entire circumference of the inner peripheral surface of the ring 40 so as to surround the liquid absorbent wick holding section 17. Alternatively, the projection section 41 can be intermittently provided in a similar manner.

[Relationship Between Projection Section 41 and Center of Gravity]

The following description discusses other configuration and effect of the ring 40.

As illustrated in FIG. 20, the ring 40 changes in thickness in the longitudinal direction of the liquid absorbent wick holding section 17. The ring 40 is thicker on a side (i.e., a right side of FIG. 20) of the protrusion section 16 than a side (i.e., a left side of FIG. 20) opposite to the side of the protrusion section 16. From this, a center of gravity of the ring 40 in the longitudinal direction of the liquid absorbent wick holding section 17 is closer to the side of the protrusion section 16. In FIG. 20, the center of gravity of the ring 40 in the longitudinal direction of the liquid absorbent wick holding section 17 is indicated by CG (Center of Gravity).

Figure 23:
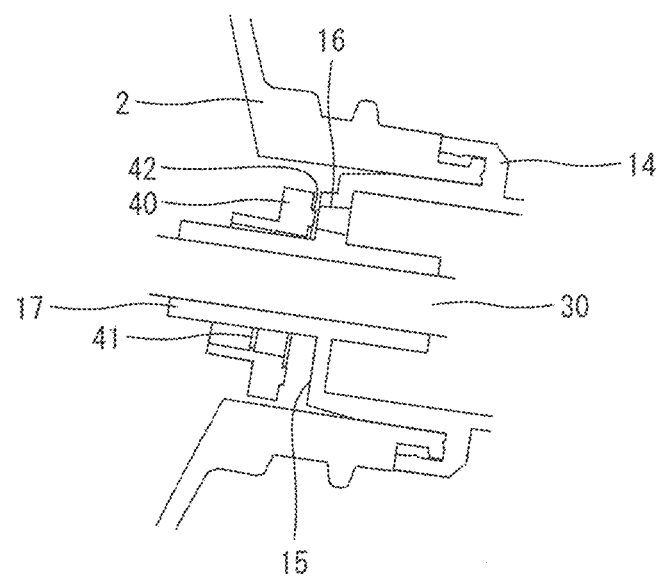
FIG. 23 is a view illustrating a state in which the ring has fallen toward the protrusion section while the protrusion section is located above the liquid absorbent wick.

The projection section 41 is provided so that the projection section 41 and the protrusion section 16 are located opposite sides of the CG. With the configuration, in a case where the suction-type liquid container 1 has fallen sideways, the ring 40 is more likely to be tilted while the projection section 41 serves as a fulcrum. Therefore, even in a case where slidability is poor between the liquid absorbent wick holding section 17 and the projection section 41, the ring 40 easily falls toward the protrusion section 16. Such a state is illustrated in FIG. 23. FIG. 23 is a view illustrating a state in which the ring 40 has fallen toward the protrusion section 16 while the protrusion section 16 is located above the liquid absorbent wick 30.

As illustrated in FIG. 23, in a case where the suction-type liquid container 1 has fallen sideways, the ring 40 (i) is easily tilted while the projection section 41 serves as a fulcrum and (ii) is thus more likely to fall toward the protrusion section 16. This makes it easy for the ring 40 to be brought closer to the through hole of the protrusion section 16. Further, the liquid stored in the container body 2 rises between the ring 40 and the flat surface 15 by the capillary action, and the through hole of the protrusion section 16 is filled with the liquid. This makes it possible to further prevent leakage of the liquid to the outside of the container body 2.

The ring 40 is thicker on the side of the protrusion section 16 than on the side opposite to the side of the protrusion section 16. Note, however, that, even in a case where another ring having a constant thickness is employed, the effect described above can be brought about by arranging the projection section 41 so that the CG is located between the projection section 41 and the protrusion section 16.

[Projection Section 42 (Second Projection Section)]

The following description discusses still other configuration and effect of the ring 40 by comparing the ring 40 with the ring 18 illustrated in FIG. 19. Note that, in the following description, surfaces of the ring 18 and the ring 40 which surfaces face the protrusion section 16 are each referred to as a facing surface.

As illustrate in FIG. 19, the entire facing surface of the ring 18 is flat. Specifically, a projection section, a groove, or the like is not provided on the facing surface of the ring 18.

Meanwhile, as illustrated in FIG. 20, a projection section 42 is provided on the facing surface of the ring 40. The projection section 42 is located at a prescribed position on the facing surface. The prescribed position means a position facing (i) the protrusion section 16 or (ii) the through hole of the protrusion section 16 in a case where the ring 40 has been brought closer to the protrusion section 16. The projection section 42 is provided so as to have a ring shape on the facing surface.

Note that the facing surface of the ring 40 can be substantially flat, except for the projection section 42. Further, a height of the projection section 42 can be minute. The projection section 42 is provided so as to be integrated with the inner peripheral surface of the ring 40 but is not limited to this.

The following description discusses an effect which is brought about by the configuration in which the ring 40 has the projection section 42 on the facing surface.

As compared with the ring 18 which does not have the projection section 42 on the facing surface, the ring 40 which has the projection section 42 projecting on the facing surface can (i) reduce a distance between the projection section 42 and the protrusion section 16 and (ii) be brought closer to the protrusion section 16 earlier. This causes the liquid stored in the container body 2 to easily permeate between the projection section 42 and the protrusion section 16, and therefore it becomes easy to suck up the liquid between the projection section 42 and the protrusion section 16. This consequently makes it possible to further prevent leakage of the liquid via the through hole provided in the protrusion section 16.

As described above, the ring 40, which is obtained by adding various features to the ring 18, makes it possible to further prevent leakage of the liquid via the through hole provided in the protrusion section 16.

[Ring 50]

Figure 24:
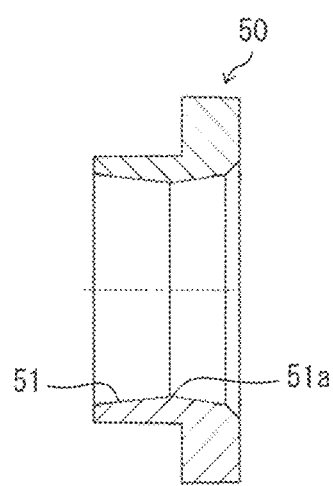
FIG. 24 is a cross sectional view illustrating still another ring in accordance with the present embodiment.

The following description discusses still another ring 50 based on comparison with the ring 18 and the ring 40. FIG. 24 is a cross sectional view illustrating the ring 50. Note that descriptions identical to those of the ring 18 and the ring 40 are not repeated.

As described above, the inner peripheral surface of the ring 18 is flat. That is, an inner diameter of the ring 18 is constant (or substantially constant), regardless of positions in the inner peripheral surface of the ring 18 in the longitudinal direction of the liquid absorbent wick holding section 17.

The ring 40 has the projection section 41 on the inner peripheral surface of the ring 40. The projection section 41 is provided throughout the entire circumference of the inner peripheral surface of the ring 40. The inner peripheral surface of the ring 40 is substantially flat, except for the projection section 41. That is, an inner diameter of the ring 40 is constant (or substantially constant), except for a part at which the projection section 41 is provided, regardless of positions in the inner peripheral surface of the ring 40 in the longitudinal direction of the liquid absorbent wick holding section 17.

Meanwhile, the ring 50 has an inclination 51 on an inner peripheral surface of the ring 50. Specifically, in the longitudinal direction of the liquid absorbent wick holding section 17, the ring 50 has an inner diameter which (i) is smallest at the peak 51*a* and (ii) becomes larger as a distance from the peak 51*a* increases (see FIG. 24).

The following description discusses an effect which is brought about by the configuration in which the inner peripheral surface of the ring 50 has the inclination 51 and the peak 51*a*.

Since the ring 50 has the inclination 51 on its inner peripheral surface, the ring 50 makes contact with the liquid absorbent wick holding section 17 via the peak 51*a*, which is a peak of the inclination 51. Therefore, in a case where the ring 50 moves toward the through hole of the protrusion section 16, it is possible for the ring 50 to have a smaller contact area with the liquid absorbent wick holding section 17, as compared with the ring 18 which makes contact with the liquid absorbent wick holding section 17 so that the inner peripheral surface of the ring 18 entirely makes contact with the liquid absorbent wick holding section 17. This allows a sliding resistance between the ring 50 and the liquid absorbent wick holding section 17 to be smaller than that between the ring 18 and the liquid absorbent wick holding section 17. Therefore, in a case where the suction-type liquid container 1 has fallen sideways, the ring 50 can (i) be brought closer to the protrusion section 16 earlier than the ring 18 or (ii) more easily fall toward the protrusion section 16 than the ring 18. Therefore, use of the ring 50 makes it possible to further prevent leakage of the liquid via the through hole provided in the protrusion section 16.

As such, as with the ring 40, the ring 50 reduces the sliding resistance between the ring 50 and the liquid absorbent wick holding section 17 by the reduced contact area with the liquid absorbent wick holding section 17. This further prevents leakage of the liquid via the through hole provided in the protrusion section 16.

Note that the configuration in which the sliding resistance with respect to the liquid absorbent wick holding section 17 is lowered by reducing the contact area with the liquid absorbent wick holding section 17 is not limited to the ring 40 and the ring 50. Alternatively, another configuration can be naturally employed, and the ring 40 and the ring 50 are merely examples of such a configuration.

[Projection Section 24 (Third Projection Section) of Liquid Absorbent Wick Holding Section 60]

The following description discusses, based on comparison with the liquid absorbent wick holding section 17, another liquid absorbent wick holding section 60 which differs from the liquid absorbent wick holding section 17. FIG. 25 is an external view illustrating the inside plug 10. (a) of FIG. 25 is a front view illustrating the inside plug 10. (b) of FIG. 25 is a bottom view illustrating the inside plug 10. Further, FIG. 26 is an external view illustrating the inside plug 10*a*. (a) of FIG. 26 is a front view illustrating the inside plug 10*a*. (b) of FIG. 26 is a bottom view illustrating the inside plug 10*a*.

As illustrated in FIGS. 25 and 26, the liquid absorbent wick holding section 60 differs from the liquid absorbent wick holding section 17 in that the liquid absorbent wick holding section 60 has projection sections 24 whereas the liquid absorbent wick holding section 17 does not have such projection section 24.

Specifically, as illustrated in (a) of FIG. 26, the liquid absorbent wick holding section 60 has two projection sections 24 which (i) extend in the longitudinal direction of the liquid absorbent wick holding section 60 and (ii) are provided on a surface of the liquid absorbent wick holding section 60 which surface faces an inner peripheral surface of a ring. As illustrated in (b) of FIG. 26, the projection sections 24 are provided so as to have a minute height on the surface of the liquid absorbent wick holding section 60 which surface faces the inner peripheral surface of the ring.

Note that each of the projection sections 24 can be either continuously or intermittently provided so as to extend in the longitudinal direction of the liquid absorbent wick holding section 60. In FIG. 24, the liquid absorbent wick holding section 60 has the two projection sections 24. Note, however, that the liquid absorbent wick holding section 60 can have one projection section 24 or three or more projection sections 24. Further, it is possible to determine as appropriate a height of each of the projection sections 24 in accordance with a distance between the inner peripheral surface of the ring and the liquid absorbent wick holding section 60.

The following description discusses an effect which is brought about by the configuration in which the liquid absorbent wick holding section 60 has the projection sections 24.

With the configuration, in a case where the ring 18 moves toward the through hole of the protrusion section 16, the projection sections 24 of the liquid absorbent wick holding section 60 make contact with the inner peripheral surface of the ring 18. This makes it possible for the ring 18 to have a smaller contact area with the liquid absorbent wick holding section 60, as compared with the case where the ring 18 makes contact with the liquid absorbent wick holding section 17. This reduces a sliding resistance between the ring 18 and the liquid absorbent wick holding section 60 and therefore, in a case where the suction-type liquid container 1 has fallen sideways, the ring 18 is more easily brought closer to the through hole of the protrusion section 16. From this, the liquid stored in the container body 2 rises between the ring 18 and the flat surface 15 by the capillary action, and thus the through hole of the protrusion section 16 is filled with the liquid. This further prevents leakage of the liquid to the outside of the container body 2.

Note that, in the description above, the ring 18 can be replaced with the ring 40 or the ring 50.

As described above, not only by employing the ring 40 or the ring 50 but also by adding features to the liquid absorbent wick holding section, it is possible to (i) reduce a contact area between the liquid absorbent wick holding section and the ring and (ii) bring about an effect of further preventing leakage of the liquid to the outside of the container body 2. The liquid absorbent wick holding section 60 is an example of such a configuration, and another configuration can be naturally employed.

[Usage]

The suction-type liquid container 1 in accordance with the present embodiment has the following usage. Note that the usage of the suction-type liquid container 1 is not limited to the following usage.

According to the suction-type liquid container 1, one end of the liquid absorbent wick 30 is soaked in the liquid stored in the container body 2 and the other end of the liquid absorbent wick 30 extends upward from the inside plug body 12.

In this case, the suction-type liquid container 1 can be incorporated into a heat evaporating/diffusing device for evaporating and diffusing a liquid from the other end of the liquid absorbent wick 30 by heating, with use of a heater or the like, the other end of the liquid absorbent wick 30 extending upward from the inside plug body 12. Alternatively, the suction-type liquid container 1 can be incorporated into a vibration spraying device for spraying a liquid from the other end of the liquid absorbent wick 30. In such a vibration spraying device, (i) a vibration plate is (a) brought into contact with the other end of the liquid absorbent wick 30 extending upward from the inside plug body 12 or (b) brought closer to the other end of the liquid absorbent wick 30 and (ii) the vibration plate is vibrated by an oscillator so that the liquid is sprayed from the other end of the liquid absorbent wick 30. Alternatively, the suction-type liquid container 1 can be incorporated into a liquid diffusing device for diffusing a liquid to an outside of the liquid diffusing device by causing the liquid to be naturally evaporated from the other end of the liquid absorbent wick 30.

As described above, the suction-type liquid container 1 is applicable to various types of usage and can prevent leakage of a liquid in any usage.

[Remarks]

The present invention can be configured in the following manners.

The inside plug in accordance with an aspect of the present invention can be configured such that the movable section is a cylindrical body; and the liquid absorbent wick holding section is fitted into the cylindrical body.

A suction-type liquid container is typically small in size, and spatial restriction on an inner space of its container body is high.

In regard to this, the movable section is a cylindrical body, and the liquid absorbent wick holding section is fitted into the cylindrical body. Therefore, the inside plug body does not need to newly include a member for attaching the movable section. This provides sufficient space at the opening of the container body at which opening the inside plug body is held, and this allows a higher degree of freedom for design such as an increase in size of the movable section.

Note that the cylindrical body means a shape which is hollow, like a tube or a pipe. Moreover, a shape of a cross section of an inner space of the cylindrical body is not limited to a particular one and may be any of various shapes such as a circular shape, a quadrangular shape, and a triangular shape.

The inside plug in accordance with an aspect of the present invention can be configured such that the movable section includes a first projection section which projects on an inner peripheral surface of the cylindrical body; and the first projection section makes contact with the liquid absorbent wick holding section in a case where the movable section has moved toward the liquid-side surface.

The following discusses a case where the movable section does not include the first projection section which projects on the inner peripheral surface of the cylindrical body. In such a case, the movable section makes contact with the liquid absorbent wick holding section so that the inner peripheral surface itself of the movable section serves as a contact surface.

Meanwhile, the following discusses a case where the movable section includes the first projection section which projects on the inner peripheral surface of the cylindrical body and the first projection section makes contact with the liquid absorbent wick holding section in a case where the movable section has moved toward the liquid-side surface. In such a case, in a case where the movable section has moved toward the liquid-side surface, the first projection section makes contact with the liquid absorbent wick holding section. This makes it possible for the movable section to have a smaller contact area with the liquid absorbent wick holding section, as compared with a case where the first projection section is not provided on the inner peripheral surface of the movable section, which is the cylindrical body.

This makes it possible to reduce a sliding resistance between the movable section and the liquid absorbent wick holding section and, in a case where the suction-type liquid container has fallen sideways, the movable section is more likely to be brought closer to the through hole. The liquid stored in the container body rises between the movable section and the liquid-side surface by the capillary action, so that the through hole provided on the liquid-side surface is filled with the liquid. This makes it possible to further prevent leakage of the liquid to an outside of the container body.

The inside plug in accordance with an aspect of the present invention can be configured such that the first projection section is provided so that the first projection section and the through hole are located opposite sides of a center of gravity of the movable section in a direction along the liquid absorbent wick holding section.

With the configuration, in a case where the suction-type liquid container has fallen sideways, the movable section is more likely to be tilted while the first projection section serves as a fulcrum. Therefore, even in a case where (i) the suction-type liquid container has fallen sideways and (ii) slidability is poor between the liquid absorbent wick holding section and the first projection section, the movable section easily falls toward the through hole. This reduces a distance between the movable section and the liquid-side surface. The liquid stored in the container body rises between the movable section and the liquid-side surface by the capillary action, so that the through hole provided on the liquid-side surface is filled with the liquid. This makes it possible to further prevent leakage of the liquid to the outside of the container body.

The inside plug in accordance with an aspect of the present invention can be configured such that the movable section includes a second projection section which projects on a surface of the movable section, the surface facing the liquid-side surface; and the second projection section is aligned such that the second projection section faces the through hole in a case where the movable section has been brought closer to the liquid-side surface.

The movable section includes the second projection section on the surface (hereinafter referred to as facing surface) facing the liquid-side surface. This allows the movable section to further reduce a distance between the second projection section and the through hole, as compared with a movable section which does not have the second projection section on the facing surface. In addition, the second projection section is aligned such that the second projection section faces the through hole in a case where the movable section has been brought closer to the liquid-side surface.

Therefore, the liquid stored in the container body rises between the movable section and the liquid-side surface by the capillary action, so that the through hole provided on the liquid-side surface is filled with the liquid. This makes it possible to further prevent leakage of the liquid to the outside of the container body.

The inside plug in accordance with an aspect of the present invention can be configured such that the liquid absorbent wick holding section includes a third projection section which projects on a surface that (i) is of the liquid absorbent wick holding section and (ii) faces an inner peripheral surface of the movable section; and the third projection section makes contact with the movable section in a case where the movable section has moved toward the liquid-side surface.

With the configuration, the third projection section makes contact with the inner peripheral surface of the movable section. Therefore, in a case where the movable section moves toward the liquid-side surface, it is possible for the movable section to have a smaller contact area with the liquid absorbent wick holding section, as compared with a liquid absorbent wick holding section which does not have the third projection section.

This reduces a sliding resistance between the movable section and the liquid absorbent wick holding section. Therefore, in a case where the suction-type liquid container has fallen sideways, the movable section is more likely to be brought closer to the through hole. As a result, the movable section can further prevent leakage of the liquid to the outside of the container body.

The inside plug in accordance with an aspect of the present invention can further includes, on the liquid-side surface, a protrusion section for facilitating separation between the liquid-side surface and the movable section.

According to the inside plug in accordance with the present invention, in a case where the suction-type liquid container has fallen sideways, the movable section is brought closer to the liquid-side surface of the inside plug body. In this case, the movable section may stick to the liquid-side surface and it may become difficult for the movable section to separate from the liquid-side surface. In a case where the movable section has stuck to the liquid-side surface so as not to separate from the liquid-side surface, the through hole provided on the liquid-side surface does not function as an air conduit. This causes the through hole not to serve a ventilation function of keeping the internal pressure of the container body stable.

With the configuration, the inside plug in accordance with the aspect of the present invention facilitates separation between the liquid-side surface and the movable section. This allows the through hole provided on the liquid-side surface to serve the ventilation function of keeping the internal pressure of the container body stable.

The inside plug in accordance with an aspect of the present invention can be configured such that the through hole passes through the protrusion section With the configuration, the inside plug in accordance with the aspect of the present invention has the protrusion section having the through hole through which the inner space of the container body communicates with outside air.

This allows the protrusion section itself to have both of (i) the ventilation function of keeping the internal pressure of the container body stable and (ii) the function of facilitating separation between the liquid-side surface and the movable section. With the configuration, it is possible to simplify a configuration of the liquid-side surface of the inside plug body.

The inside plug in accordance with an aspect of the present invention can be configured such that the movable section is made of a material different from that of the liquid absorbent wick holding section.

The movable section is brought into closer to the liquid-side surface in a case where the suction-type liquid container has fallen sideways.

In regard to this, since the movable section is made of a material different from that of the liquid absorbent wick holding section, the movable section can have higher mobility and slidability with respect to the liquid absorbent wick holding section. For example, the movable section is made of a material which (i) has specific gravity higher than that of the liquid stored in the suction-type liquid container and (ii) differs from the material of the liquid absorbent wick holding section.

The inside plug in accordance with an aspect of the present invention can be configured such that the movable section has a ring shape; and the liquid absorbent wick holding section is fitted inside an inner periphery of the movable section.

A suction-type liquid container is typically small in size, and spatial restriction on an inner space of its container body is high.

In regard to this, the movable section has a ring shape, and the liquid absorbent wick holding section is fitted into the inner periphery of the movable section. Therefore, the inside plug body does not need to newly include a member for attaching the movable section. This provides sufficient space at the opening of the container body at which opening the inside plug body is held, and this allows a higher degree of freedom for design such as an increase in size of the movable section.

A suction-type liquid container in accordance with an aspect of the present invention can include an inside plug of any one of the aspects.

This makes it possible to provide a user with a suction-type liquid container which brings about the above described various effects.

The present invention is not limited to the embodiments, but can be altered by a skilled person in the art within the scope of the claims. An embodiment derived from a proper combination of technical means each disclosed in a different embodiment is also encompassed in the technical scope of the present invention.

INDUSTRIAL APPLICABILITY

The present invention relates to an inside plug and is applicable to a suction-type liquid container.

REFERENCE SIGNS LIST

1: Suction-type liquid container
2: Container body
3: Outside plug
10: Inside plug
12: Inside plug body
14: Bottle plug
15: Flat surface (liquid-side surface)
16: Projection section
17, 60: Liquid absorbent wick holding section
18, 40, 50: Ring (movable section)
20: Ring stopping section
22: Liquid discharge hole
24: Projection section (third projection section)
30: Liquid absorbent wick
41: Projection section (first projection section)
42: Projection section (second projection section)
51: Inclination
51a: Peak

The invention claimed is:

1. An inside plug for holding, at an opening of a container body of a suction-type liquid container, a liquid absorbent wick for sucking up a liquid stored in the container body, said inside plug being inserted in the container body, said inside plug comprising:
an inside plug body which is held at the opening;
a liquid absorbent wick holding section for holding the liquid absorbent wick, the liquid absorbent wick holding section being connected to the inside plug body; and
a movable section which (i) is located in an inner space of the container body in a state where the inside plug body is held at the opening and (ii) is movable in a direction along the liquid absorbent wick holding section,
the inside plug body having, on a liquid-side surface thereof, a through hole through which the inner space of the container body communicates with outside air, the liquid-side surface being a surface of the inside plug body and being located on a side of the liquid stored in the container body, and
the movable section being brought closer to the liquid-side surface by gravity in a case where the suction-type liquid container has fallen sideways, wherein:
the movable section is a cylindrical body; and
the liquid absorbent wick holding section is fitted into the cylindrical body.

2. The inside plug as set forth in claim 1, wherein:
the movable section includes a first projection section which projects on an inner peripheral surface of the cylindrical body; and
the first projection section makes contact with the liquid absorbent wick holding section in a case where the movable section has moved toward the liquid-side surface.

3. The inside plug as set forth in claim 2, wherein the first projection section is provided so that the first projection section and the through hole are located opposite sides of a center of gravity of the movable section in a direction along the liquid absorbent wick holding section.

4. The inside plug as set forth in claim 1, wherein:
the movable section includes a second projection section which projects on a surface of the movable section, the surface facing the liquid-side surface; and
the second projection section is aligned such that the second projection section faces the through hole in a case where the movable section has been brought closer to the liquid-side surface.

5. The inside plug as set forth in claim 1, wherein:
the liquid absorbent wick holding section includes a third projection section which projects on a surface that (i) is of the liquid absorbent wick holding section and (ii) faces an inner peripheral surface of the movable section; and
the third projection section makes contact with the movable section in a case where the movable section has moved toward the liquid-side surface.

6. The inside plug as set forth in claim 1, further comprising, on the liquid-side surface, a protrusion section for facilitating separation between the liquid-side surface and the movable section.

7. The inside plug as set forth in claim 6, wherein the through hole passes through the protrusion section.

8. The inside plug as set forth in claim 1, wherein the movable section is made of a material different from that of the liquid absorbent wick holding section.

9. A suction-type liquid container comprising an inside plug recited in claim 1.

10. An inside plug for holding, at an opening of a container body of a suction-type liquid container, a liquid absorbent wick for sucking up a liquid stored in the container body, said inside plug being inserted in the container body,
said inside plug comprising:
an inside plug body which is held at the opening;
a liquid absorbent wick holding section for holding the liquid absorbent wick, the liquid absorbent wick holding section being connected to the inside plug body; and
a movable section which (i) is located in an inner space of the container body in a state where the inside plug body is held at the opening and (ii) is movable in a direction along the liquid absorbent wick holding section,
the inside plug body having, on a liquid-side surface thereof, a through hole through which the inner space of the container body communicates with outside air, the liquid-side surface being a surface of the inside plug body and being located on a side of the liquid stored in the container body, and the movable section being brought closer to the liquid-side surface by gravity in a case where the suction-type liquid container has fallen sideways, wherein:
the movable section has a ring shape; and
the liquid absorbent wick holding section is fitted inside an inner periphery of the movable section.

* * * * *